(12) United States Patent
Song

(10) Patent No.: US 11,497,611 B1
(45) Date of Patent: Nov. 15, 2022

(54) HIP IMPLANT DEVICE

(71) Applicant: Omnes Medical Inc., Houston, TX (US)

(72) Inventor: Benjamin Sooil Song, Los Angeles, CA (US)

(73) Assignee: Omnes Medical, Inc., Houston, TX (US)

( * ) Notice: Subject to any disclaimer, the term of this patent is extended or adjusted under 35 U.S.C. 154(b) by 429 days.

(21) Appl. No.: 16/568,085

(22) Filed: Sep. 11, 2019

(51) Int. Cl.
*A61F 2/34* (2006.01)
*A61F 2/36* (2006.01)
*A61F 2/30* (2006.01)

(52) U.S. Cl.
CPC .............. *A61F 2/34* (2013.01); *A61F 2/3609* (2013.01); *A61F 2/3094* (2013.01); *A61F 2/30767* (2013.01); *A61F 2/3601* (2013.01); *A61F 2002/3652* (2013.01); *A61F 2220/0033* (2013.01); *A61F 2310/00023* (2013.01); *A61F 2310/00029* (2013.01); *A61F 2310/00059* (2013.01)

(58) Field of Classification Search
CPC ...... A61F 2/34; A61F 2/3609; A61F 2/30767; A61F 2/3094; A61F 2/3601; A61F 2002/3652; A61F 2220/0033; A61F 2310/0023; A61F 2310/0029; A61F 2310/00059
See application file for complete search history.

(56) References Cited

U.S. PATENT DOCUMENTS

| | | | |
|---|---|---|---|
| 6,616,697 B2 * | 9/2003 | Sotereanos | A61F 2/3601 623/23.26 |
| 8,840,675 B2 | 9/2014 | Song | |
| 9,782,206 B2 * | 10/2017 | Mueckter | A61B 17/725 |
| 2010/0174380 A1 * | 7/2010 | Lewis | A61F 2/32 623/22.11 |
| 2014/0188240 A1 * | 7/2014 | Lang | A61F 2/3609 623/22.12 |

OTHER PUBLICATIONS

A.J. Wassef et al., "Use of an offset head center acetabular shell in difficult primary total hip arthroplasties", Annals of Translational Medicine, 2019, 7(4):75, 7 pages.

(Continued)

*Primary Examiner* — Jennifer Dieterle
*Assistant Examiner* — Christine L Nelson
(74) *Attorney, Agent, or Firm* — Mark Protsik; Thomas Schneck

(57) ABSTRACT

A hip implant is provided that includes a metal acetabular cup to be inserted into an acetabulum of the pelvis, a femoral head and neck portion with a polymer femoral head molded onto a metal formal head base that is attached to a metal femoral neck rod configured to be inserted into the neck of a femur, and a metal main body shaft configured to be inserted into a femoral shaft region of the femur and secured by bone screws. The head base may have stabilizing features, such as dimples and peripheral mounds, over which the femoral head is molded. The main body shaft also has diagonal hole located at the center line of the neck of the femur to receive the femoral neck rod at an adjustable angle. The femoral head interfaces with the acetabular cup as a smooth plastic-to-metal spherical-surface joint.

15 Claims, 26 Drawing Sheets

(56) References Cited

OTHER PUBLICATIONS

M. Scaglione et al., "Hip replacement inn femoral head osteonecrosis: current concepts", Clinical Cases in Mineral and Bone Metabolism 2015, 12(Suppl. 1), pp. 51-54, 4 pages.

K. Issa et al., "Hip pathologies that bedevil—Osteonecrosis of the femoral head: The total hip replacement solution", CCJR Supplemental to the Bone & Joint Journal, vol. 95-B, No. 11, Nov. 2013, pp. 46-50, 5 pages.

* cited by examiner

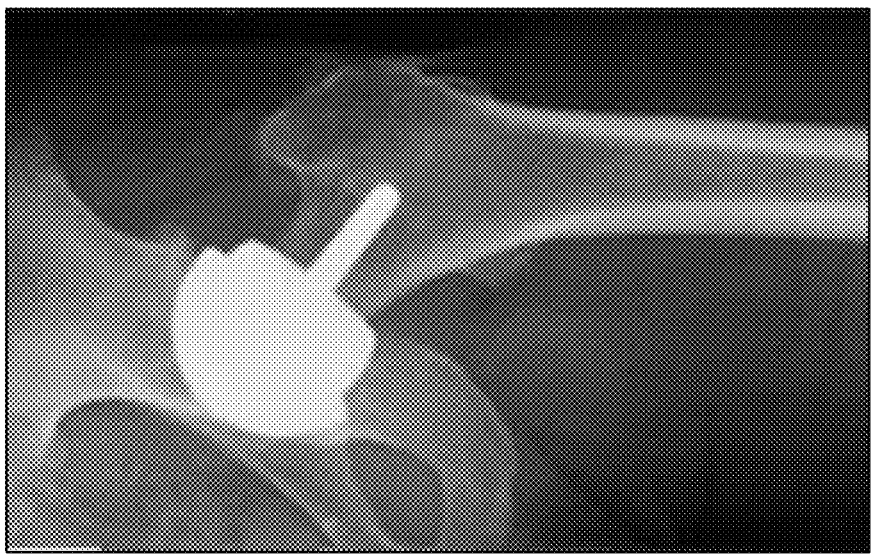
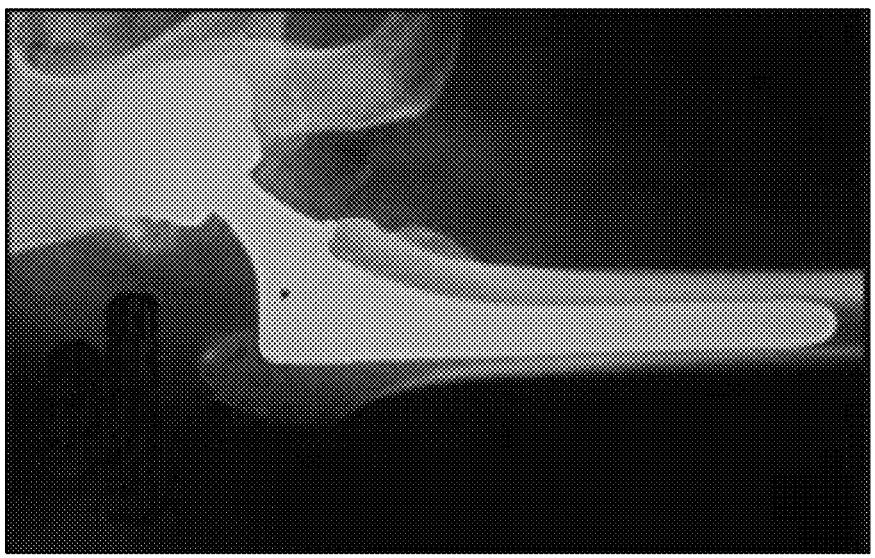
Hip Resurfacing Implant
Mini Hip Implant
Standard Hip Implant
FIG. 1
(Prior Art)

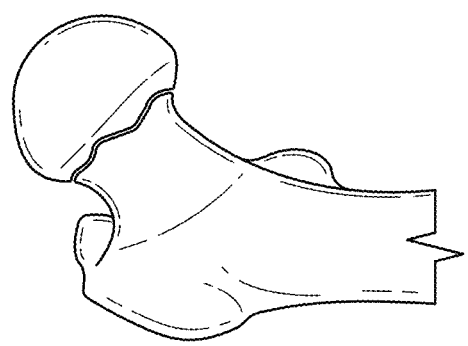
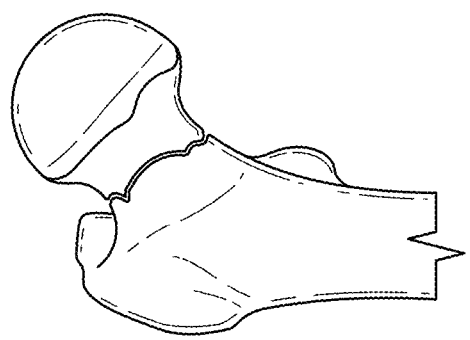
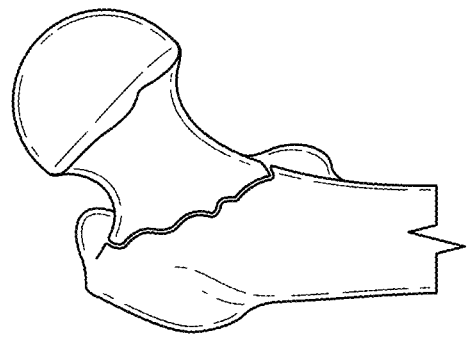
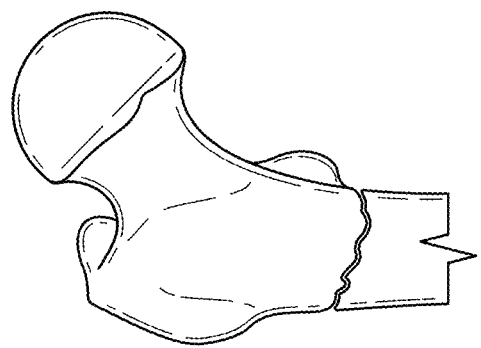
FIG. 2

$$\phi = \angle ao_1b = \angle ao_1c$$
$$R = \overline{bo_1} = \overline{co_1}$$

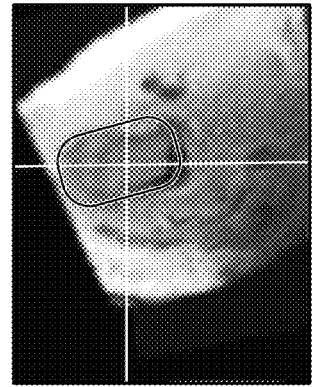
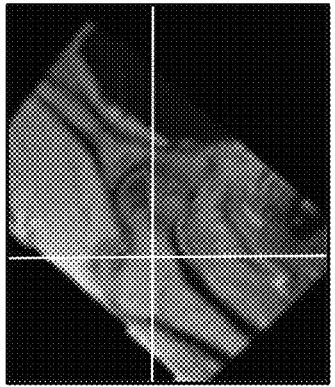
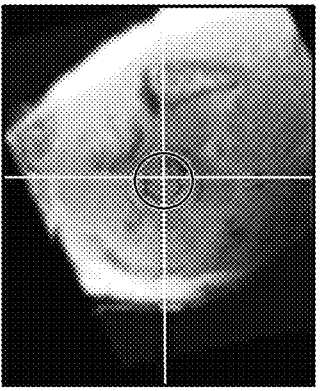
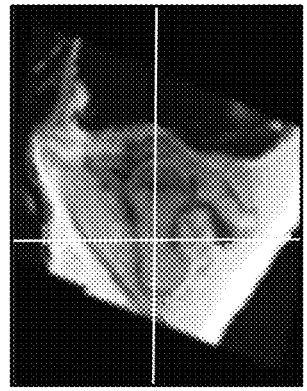
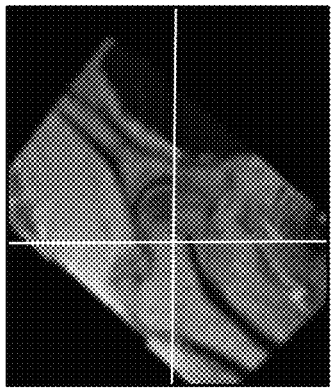
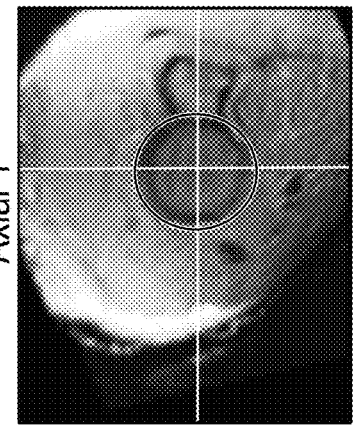
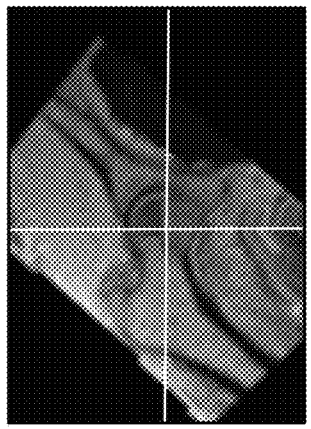
FIG. 16

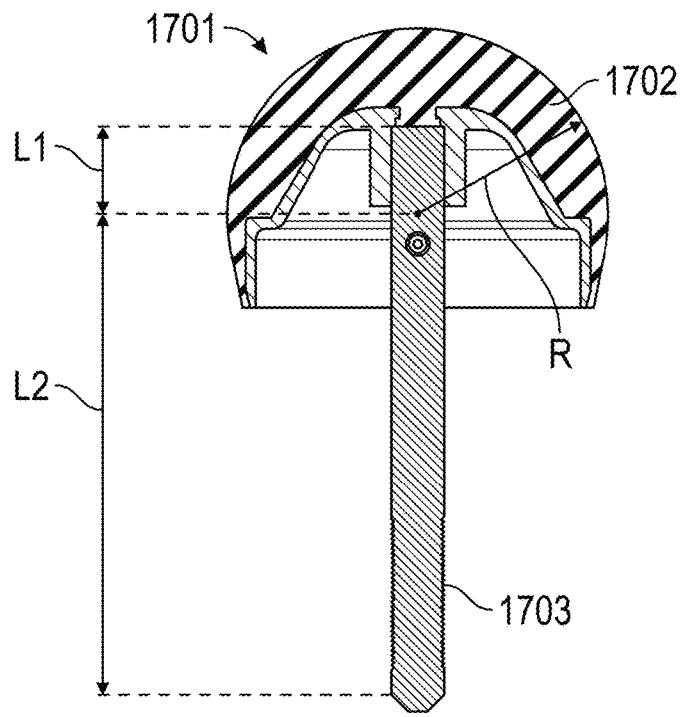
FIG. 17
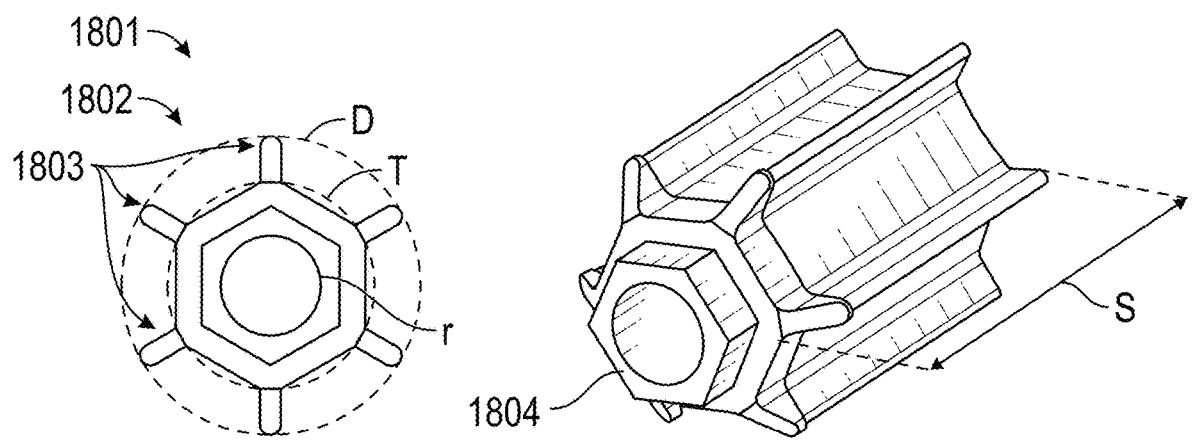
FIG. 18A  FIG. 18B

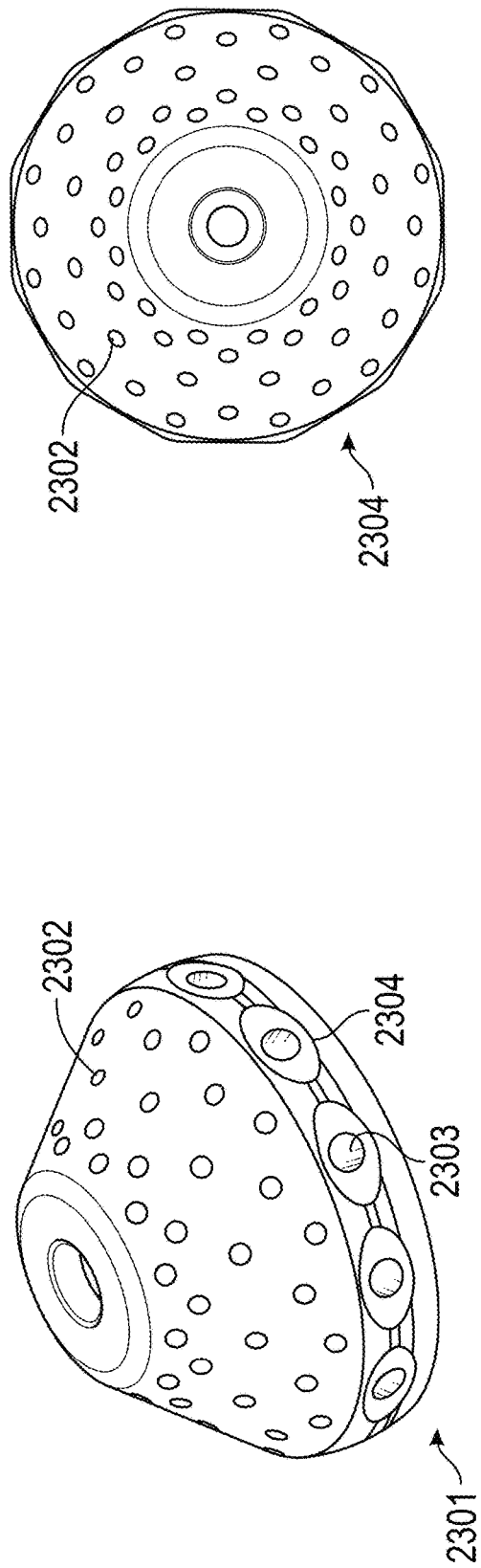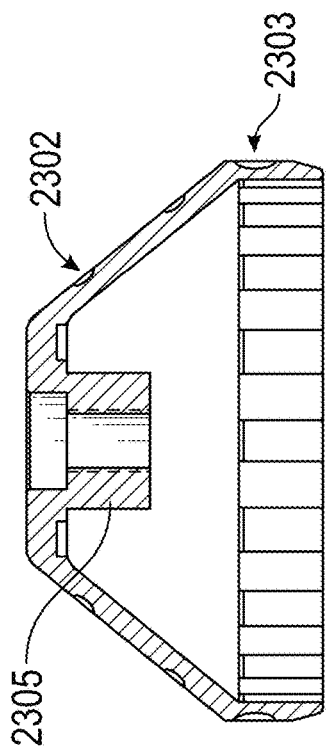
FIG. 25B
FIG. 25C
FIG. 25A

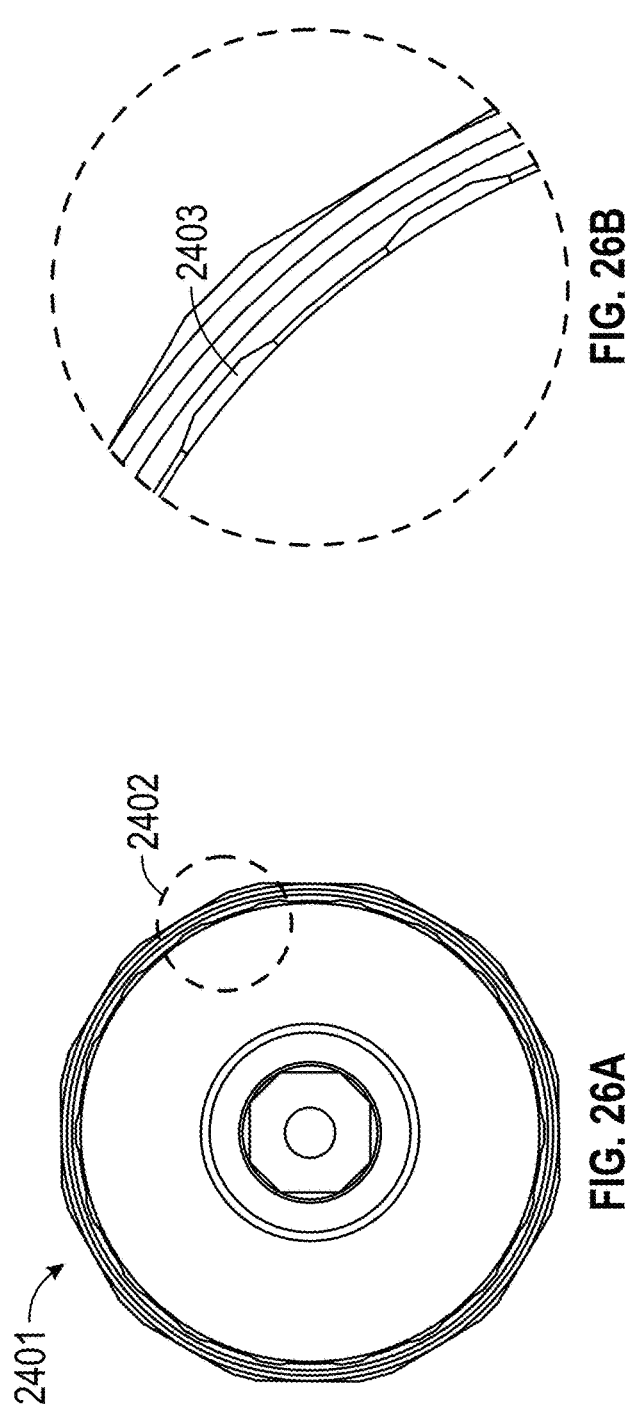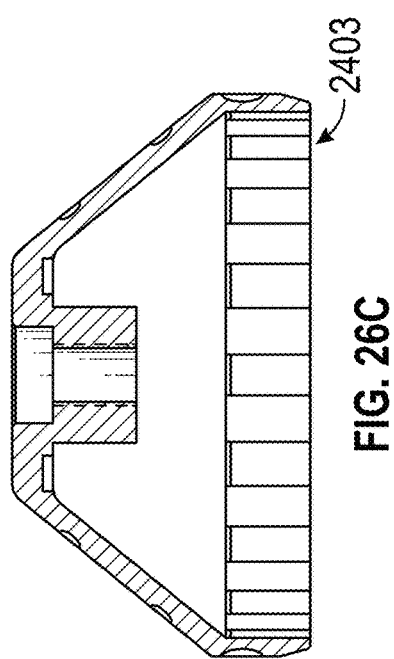

HIP IMPLANT DEVICE

TECHNICAL FIELD

The present invention relates to hip implants for the acetabular-femoral joint.

BACKGROUND ART

U.S. Pat. No. 8,840,675 to Song describes a "minimal invasive" hip arthroplasty device comprising a long nail portion, a lag screw portion, and a resurfacing head interfacing with an acetabular cup. The long nail portion is inserted into the shaft of the femur. Distal locking screws fix the long nail portion to the femur. The lag screw portion inserts into the neck of the femur and into a lag screw hole of the long nail portion. A set screw within the hollow long nail portion engages with locking grooves on the lag screw portion. The resurfacing head screws into a hole in the neck end of the lag screw portion.

In implant devices of this type, both the acetabular cup and resurfacing head were, at one time, both made of bio-compatible metals for a metal-to-metal joint. However, this combination generated metallic particles during use to the detriment of the implant recipient's health, and therefore such metal-to-metal joints are no longer permitted. Replacing the metallic acetabular cup with one made of thick bio-compatible polymer material resulted in considerably more wear during use. Over time, the relatively smaller femoral head wore down the cup surface until it no longer fit properly within the cup, resulting in dislocations.

A further complication of implant devices of this type are that a three-piece construction is surgically implanted most easily when drilling for the lag screw portion is done from two sides, both through the femoral neck and also through the side of the femoral shaft (where the relatively shorter distance to the long nail portion can help ensure that the lag screw hole in the long nail portion is in the proper position in the femoral shaft for accepting the lag screw portion coming from the femoral neck). However, drilling from two sides does not guarantee that the two drill holes will align.

FIG. 1 shows several existing prior art hip implants, i.e., standard, mini and resurfacing implants. The standard implant requires the removal (bone resection) of the entire femoral neck and head. Furthermore, with existing standard implants, the femoral neck angle of hip implant is fixed; thus, it could cause misalignment if it differs significantly from the original femoral neck angle. The mini implant requires the resection to be located approximately in the middle of the femoral neck, resulting in the removal of the femoral head and approximately half of the femoral neck. As a result, the mini hip implant can be used for those who have good cortical and cancellous bone integrity of reasonably strong bone strength and density. On the other hand, the resurfacing implant requires the surface removal of part of the femoral head only to make the implant placed on the femoral head. The current hip resurfacing implant includes metal to metal contact, and any contact debris can cause serious health problems. Also, the resurfacing implant requires reasonably strong bone strength and high density.

FIG. 2 shows several types of femoral fracture commonly occurring in the femoral neck area, i.e., subcapital neck fracture, transcervical neck fracture, intertrochanteric fracture and subtrochanteric fracture. The subcapital neck fracture takes place on the boundary of the femoral neck and head. The transcervical neck fracture occurs approximately in the middle of the femoral neck. Additionally, an intertrochanteric fracture can occur at the root of the femoral neck. As shown in FIG. 1, the benefit of the resurfacing implant is to preserve of all anatomical information of patients. However, the resurfacing hip implant is susceptible to these three types of fracture; whereas the mini hip implant is only susceptible to the intertrochanteric fracture. Thus, the resurfacing implant should only be used for young patients who still have strong bone quality. The mini implant, however, is susceptible to the intertrochanteric fracture; so, it requires strong fusion between the cancellous and implant surfaces. Consequently, this implant is also commonly used only on relatively young patients. Still further, the standard hip implant can cause a subtrochanter fracture during or after the surgery, which occurs along the femoral stem just below the root of the femoral neck. Additionally, the resection position for the standard implant can result in malposition of the artificial femoral head center due to a loss of anatomical center position.

SUMMARY DISCLOSURE

The present invention introduces a resurfacing implant that preserves most anatomic characteristics, such as femoral neck and partial head, while reinforcing the femoral neck area to increase the internal strength to prevent all three types of fracture from occurring. Also, the contact between the femoral head and acetabular cup is plastic-to-metal to avoid generating any debris caused by metal-to-metal contact, where the plastic joint surface is a thick polymer coating over metal on the femur side, while the metal forms a thin cup on the hip side (i.e. the acetabular cup).

In particular, a hip implant in accord with the present invention generally comprises an acetabular cup, a femoral head and neck portion, and a main body shaft. The acetabular cup is configured to be inserted into an acetabulum anatomy of a pelvis and is composed of a bio-compatible metal. The femoral head and neck portion has a femoral head composed of a bio-compatible polymer molded onto a bio-compatible metal femoral head base that is attached to a bio-compatible metal femoral neck rod. The femoral head is configured to interface with the acetabular cup as a smooth plastic-to-metal spherical-surface joint. The femoral neck rod is configured to be inserted along a center line into a neck of the femur. The main body shaft is configured to be inserted into a femoral shaft region of femur and secured by bone screws through cortical bone of the femur. The main body shaft is composed of a bio-compatible metal and has a linear central axis that extends an entire length of the main body shaft. It also has a zigzag-shaped diagonal hole therethrough that is located at the center line of the neck of the femur so as to receive the femoral neck rod at an adjustable angle to align with the center line of the neck.

In an alternative embodiment, the metal femoral head base can have stabilization features that enhance binding of the plastic joint surface of the femoral head onto that base for a secure femoral head construction. For example, the femoral head base may have dimples and peripheral mounds over its surface to create a stable interface with the polymer head.

BRIEF DESCRIPTION OF THE DRAWINGS

FIG. 1 a side x-ray images showing standard, mini, and resurfacing implants of the prior art.

FIG. 2 a side views illustrating four common types of femoral neck fractures.

FIG. 16 is a set of MRI slices in coronal, axial, sagittal views at the femoral head, near the impinging line and approaching the greater trochanter to lesser trochanter zones.

FIG. 17 is a side sectional view illustrating dimensions of the femoral head part.

FIGS. 18A and 18B are end and perspective views of a reinforcer component for the femoral neck.

FIG. 25A is a perspective view of a metallic base of an alternative femoral head part of an implant in accord with the invention.

FIG. 25B is a top view of the femoral head base of FIG. 25A.

FIG. 25C is a cross-sectional view of the femoral head base of FIG. 25A.

FIG. 26A is a bottom view of the femoral head base of FIG. 25A.

FIG. 26B is an enlarged bottom view of a peripheral portion of the femoral head base of FIG. 26A.

FIG. 26C is a cross-sectional view of the femoral head base of FIG. 26A.

DETAILED DESCRIPTION

Figure 3A:
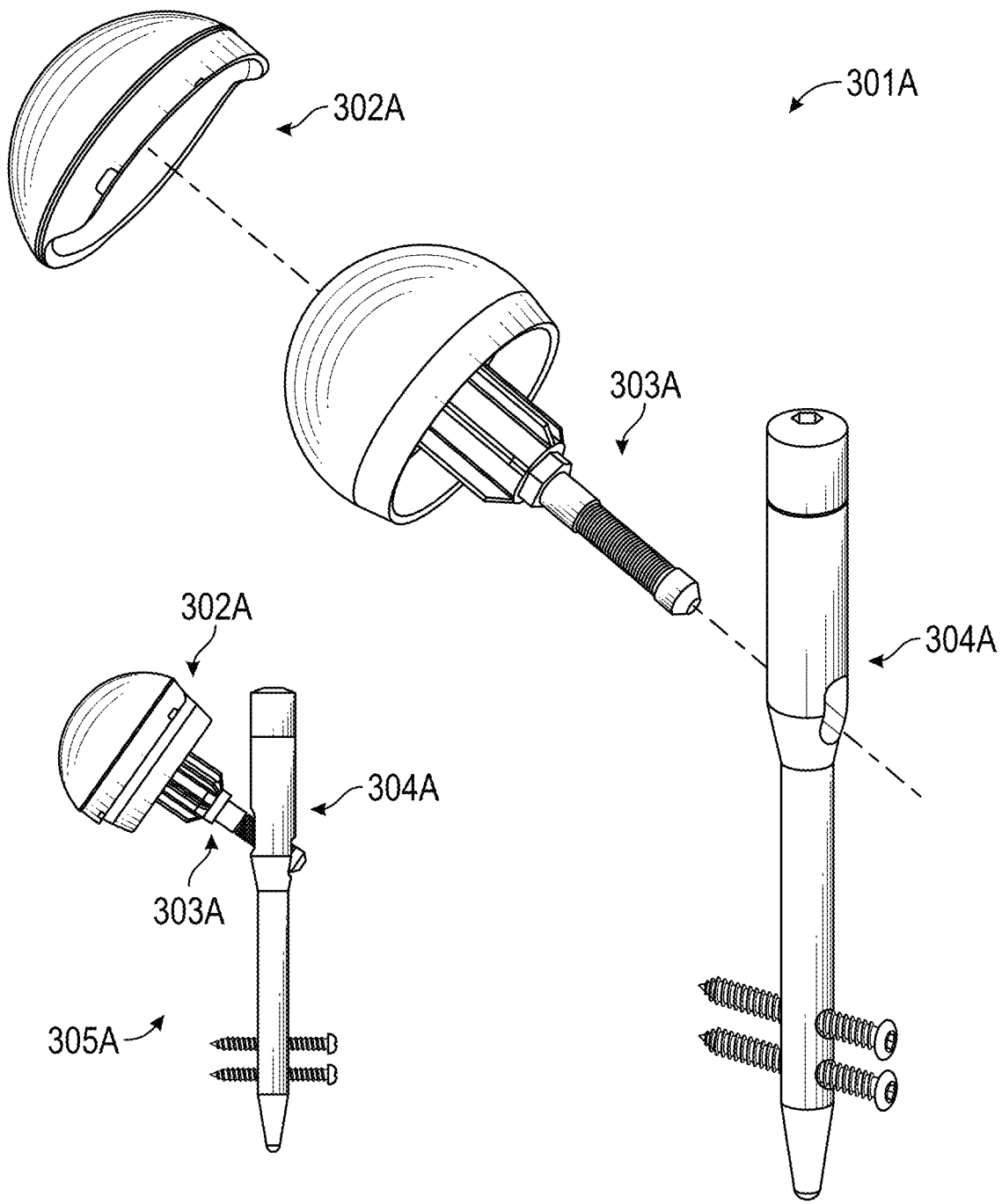
FIG. 3A is a perspective view of side-by-side assembled and exploded embodiments of the present invention.

FIG. 3A shows the assembled view 305A and exploded view 301A of an embodiment of the current invention. The implant consists of the three portions: an acetabular cup 302A, a femoral head and neck 303A and a main body shaft 304A.

The design for this implant uses only bio-compatible materials, such as polyethylene, polyether ether ketone (PEEK) or ultra-high-molecular-weight polyethylene (UHMWPE), and bio-compatible metal, such as cobalt, chromium, titanium, alloys thereof, or medical-grade stainless steel 316.

Figure 3B:
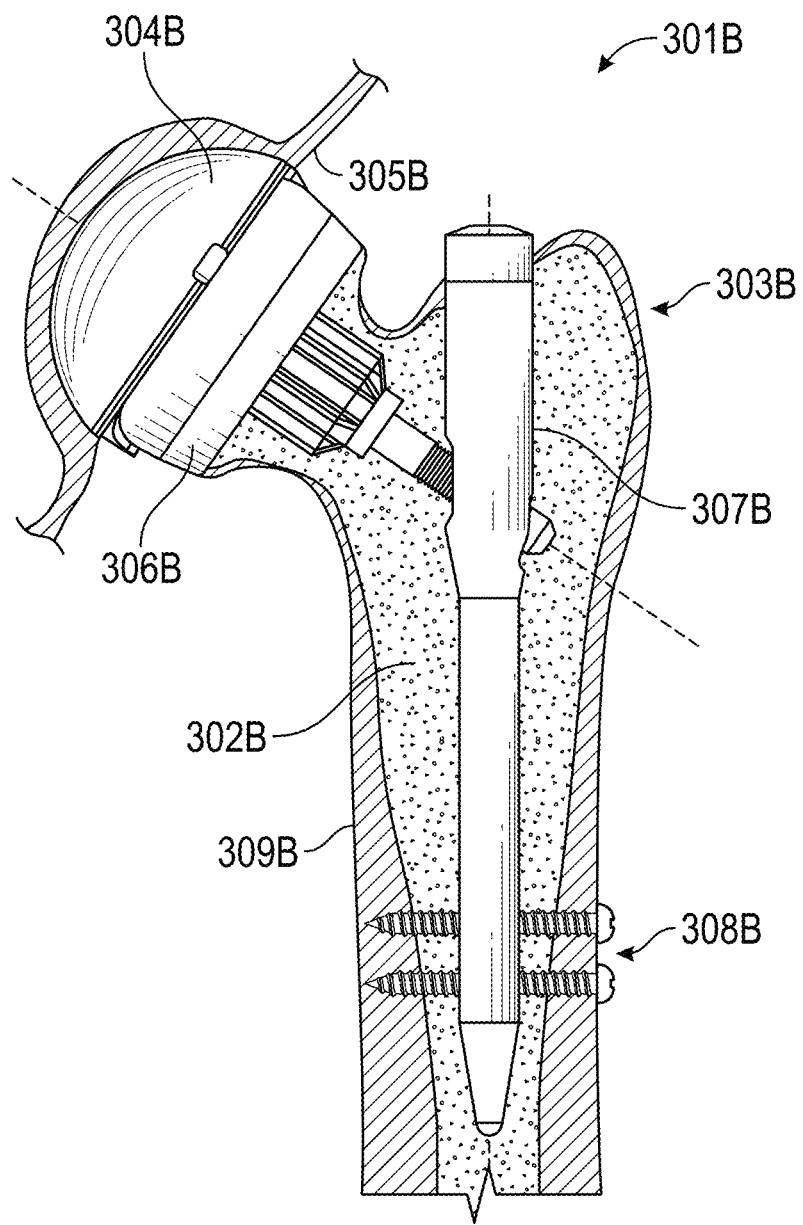
FIG. 3B is a coronal sectional view of resurfacing hip implant of the present invention.

FIG. 3B shows a coronal view 301B of the resurfacing hip implant of the invention 302B, which shows the anatomically positioning in the proximal femur 303B. The acetabulum implant cup 304B is inserted into the hip's acetabulum anatomy 305B. The femoral head and neck 306B and the main body shaft 307B are inserted into the proximal femur 303B. Bone screws 308B secure the main body shaft 307B at the femoral shaft region through the cortical bone 309B from lateral to medial direction.

Figure 4C:
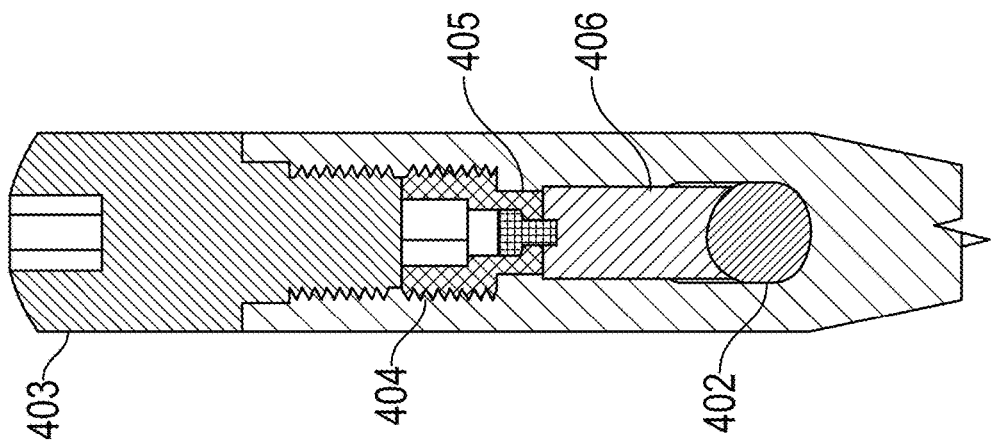
FIGS. 4A, 4B and 4C are respective side, sectional, and close-up views of an assembled main body shaft component of the implant of FIG. 3A.
Figure 4B:
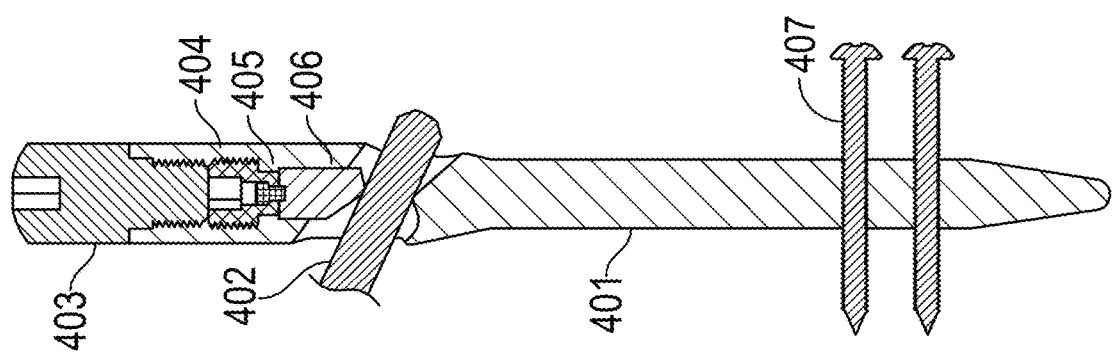
Figure 4A:
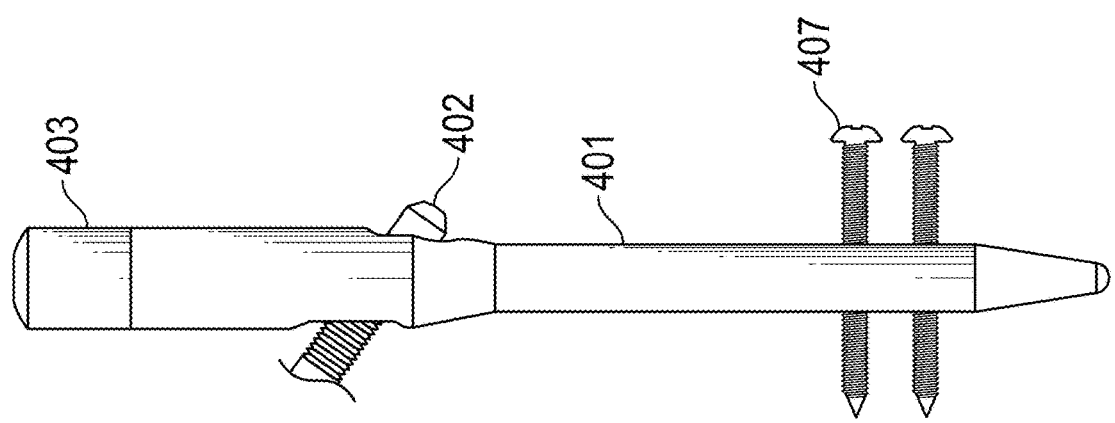

FIGS. 4A-4C show a main body shaft 401 assembled view, a cross-sectional view, and a close view of the secured lock mechanism. A connecter 405 loosely connects a collar 404 to the angle adjustment joint mechanism 406. The collar 404 is screwed down to push an angle adjustment joint mechanism 406 into the main shaft part 401 and fits the angle adjustment joint mechanism to the femoral neck rod 402. Bone screws 407 fit the main body shaft 401 into the cortical bone. In order to further secure the main body shaft 401, a top cover 403 is screwed down to push upon the top surface of the collar 404. As a result, double screwing of the top cover 403 and collar 404 lead to securing the connection between the femoral neck rod 402 and main body shaft 401.

Figure 5:
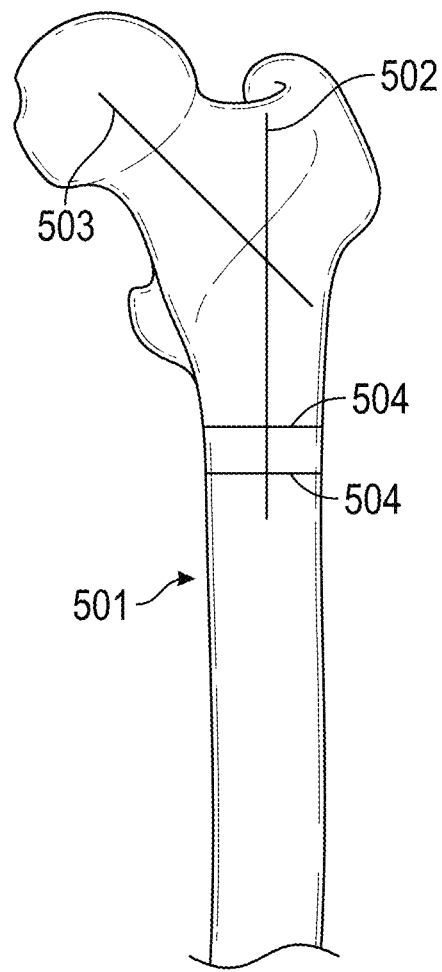
FIG. 5 is a side view showing the implant features reinforcing areas of the proximal femur vulnerable to fracture.

FIG. 5 shows how this design supports all areas of the proximal femur 501 that are vulnerable to the various fractures illustrated in FIG. 2. Femoral neck rod 503 reinforces the femoral neck in the proximal femur to significantly lower the chance of a subcapital neck fracture and transcervical neck fracture. Furthermore, the interlocking feature of the femoral neck rod 503 and main body shaft 502 can prevent the bone from any intertrochanteric fractures. And, the bone screws 504 inserted into the main body shaft 502 in the bone shaft region diminish the chance of a subtrochanteric fracture.

Figure 6D:
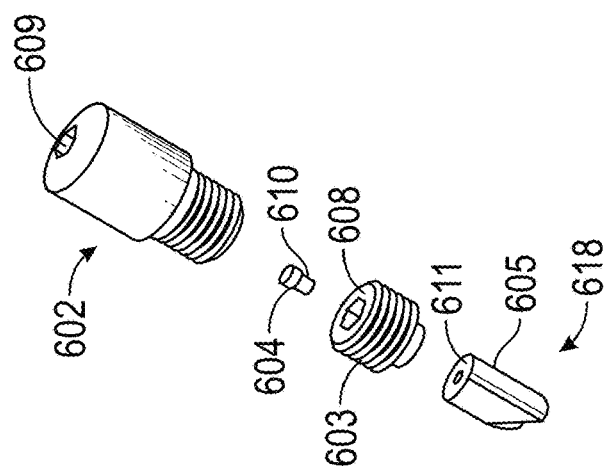
FIGS. 6A-6D are perspective, right, front and exploded views, respectively, of a secured lock mechanism of the main body shaft.
Figure 6C:
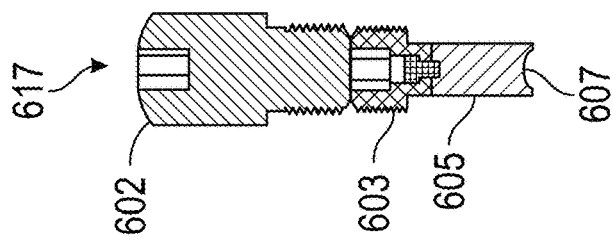
Figure 6B:
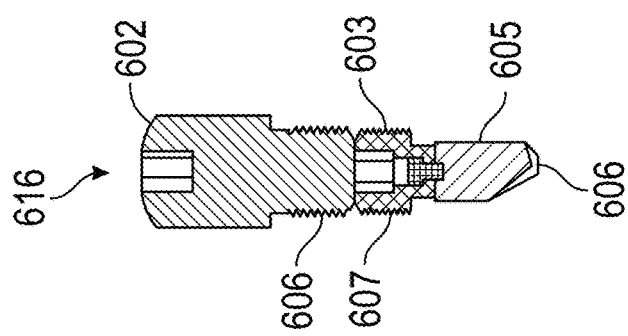
Figure 6A:
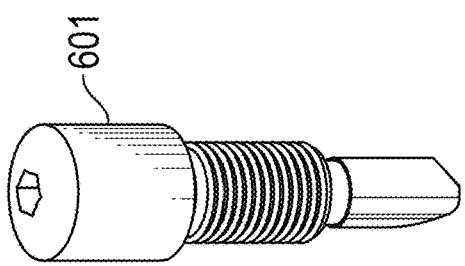

FIGS. 6A-6D show the secured lock mechanism 601 in perspective (FIG. 6A), right view (FIG. 6B), front view (FIG. 6C) and the exploded view (FIG. 6D). The inside of the main body shaft has been threaded to have the secured lock mechanism tight inside. The outside of collar 603 and cap secured lock 602 have been threaded 607 and 606 to be fixed inside the shaft. The connecter screw 604 loosely connects the collar into the angle adjustment joint mechanism 605. Later the cap lock closes the main body shaft and presses the collar into the angle adjustment joint mechanism. The Allen wrench 609 is used to fully tighten the angle adjustment joint mechanism (double secured).

Figure 7A:
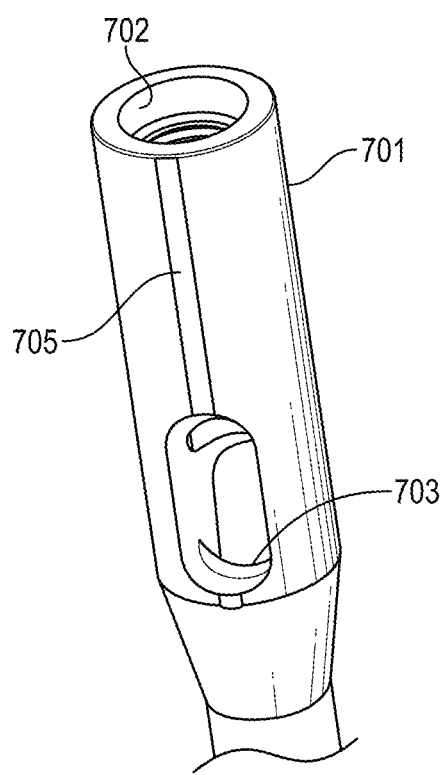
FIGS. 7A and 7B are perspective and cutaway views of the diagonal hole in the main body shaft that receives the femoral neck rod.
Figure 7B:
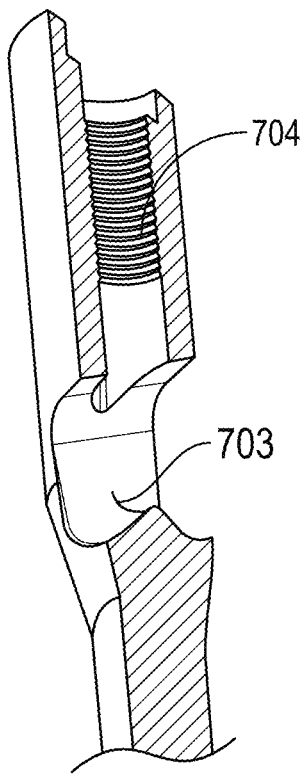

FIGS. 7A and 7B show the main shaft body 701 with interior female threads 704 and which fits the secured lock mechanism. The curved shape hole 703 is designed to accommodate different angles of the femoral neck rod. Top cover secured lock and the collar are screwed into the shaft by means of female threading 704 inside the shaft. After fixing the angle of the femoral neck rod and main body shaft 701, the secured lock mechanism is pressed into the femoral neck rod. The flat feature 705 is a direction indicator that represents medial positioning of the main body shaft 701 during the surgery.

Figure 8A:
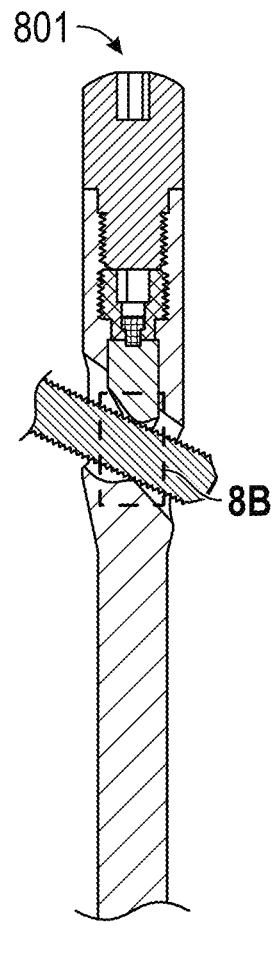
FIGS. 8A and 8B are a sectional view and close-up view of the diagonal hole with the angle adjustment joint mechanism engaging the femoral neck rod.
Figure 8B:
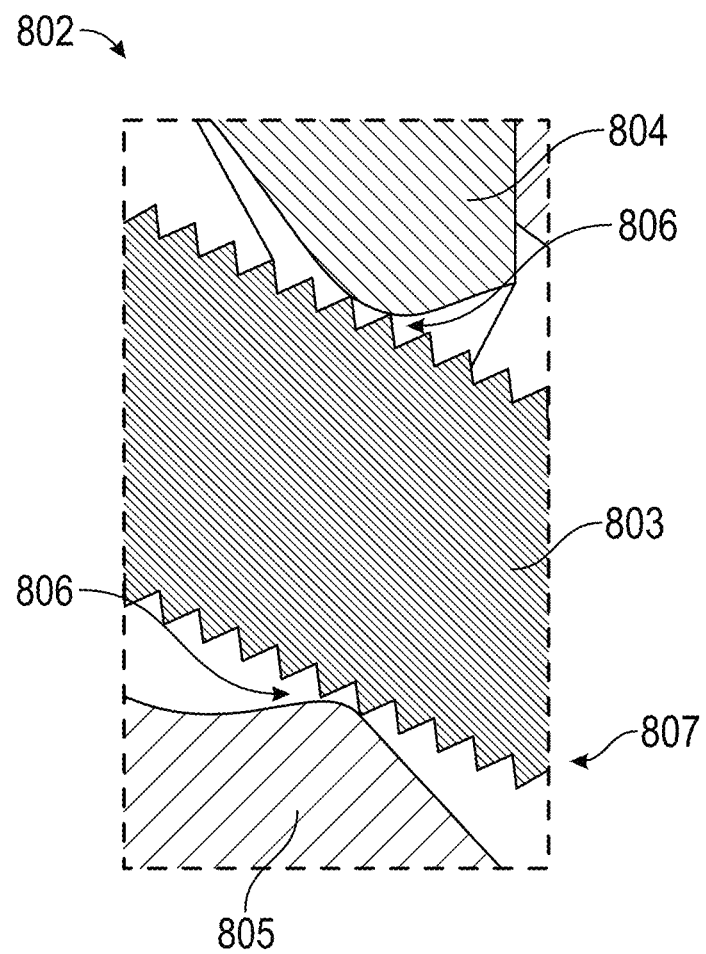

FIGS. 8A and 8B show the "angle adjustment joint mechanism" 802 to adjust the angle between the femoral neck rod 803 and the implant femoral main body shaft 805. This mechanism allows adjusting the angle based on the patient's personal anatomy. As can be seen in the cross section of the angle adjustment mechanism 807, the zigzag shape stabilizes the femoral neck into the femoral shaft. After securing the femoral stem the "angle adjustment joint mechanism" is fitted into the "femoral stem" by screw down to the zigzag-shaped stop 806. The top cover secured lock 801 and collar are screwed down and crushes the zigzags in the contact area and makes a tiny surface penetration between femoral neck rod 803 and angle adjustment joint mechanism. The connection between the femoral neck rod into the main body shaft is stabilized.

The angle adjustment mechanism 802 is responsible for adjusting the angle between femoral neck rod 803 and the femoral main body shaft 805. This angle varies from patient to patient. The femoral neck will be fixed in the angle adjustment hole by means of the collar screw and top cover secured lock.

Figure 9:
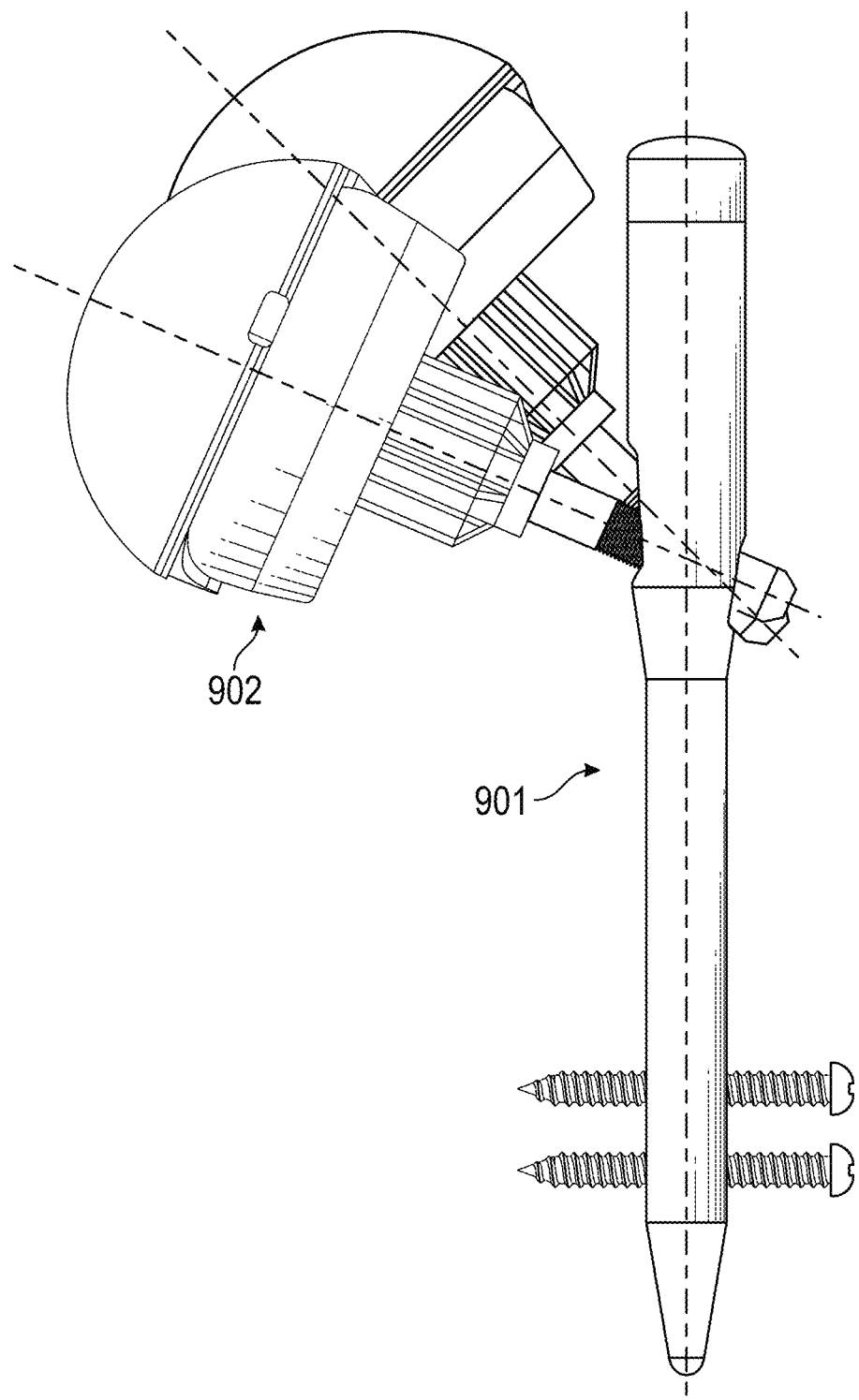
FIG. 9 is a side view with the head and neck portion in three possible angular orientations relative to the main body shaft.

As shown in FIG. 9, the angle between main body shaft 901 and the femoral neck rod 902 accommodates a range of angles from 40° to 70°. Consequently, the novel curved hole enables the surgeon to adjust the angle relative to the main body shaft in a range of 110° to 140°. A more vertical 140° angle is believed to be typical for most patients. Providing a range of angles will accommodate the need for various joint angles for all age groups and prevent any joint misalignment problem.

Figure 10A:
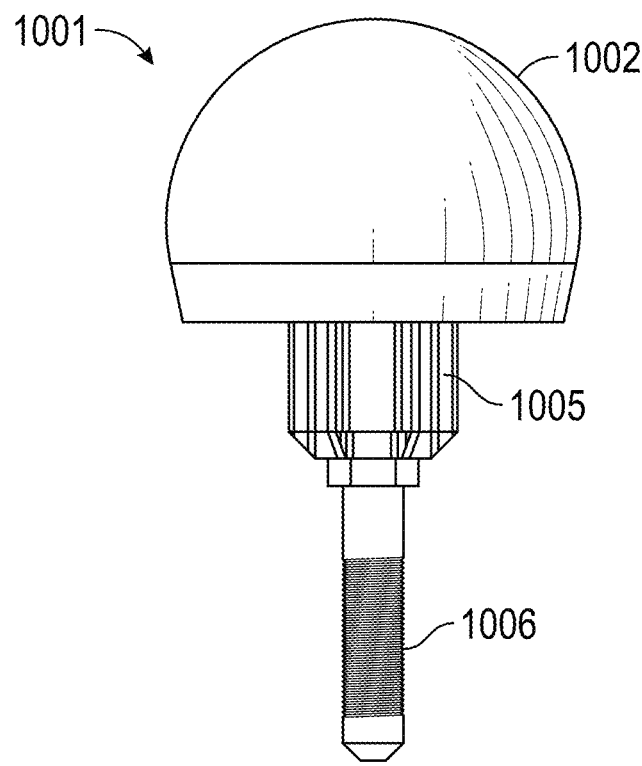
FIGS. 10A and 10B are side and cross-sectional views of the femoral head and neck parts of the implant.
Figure 10B:
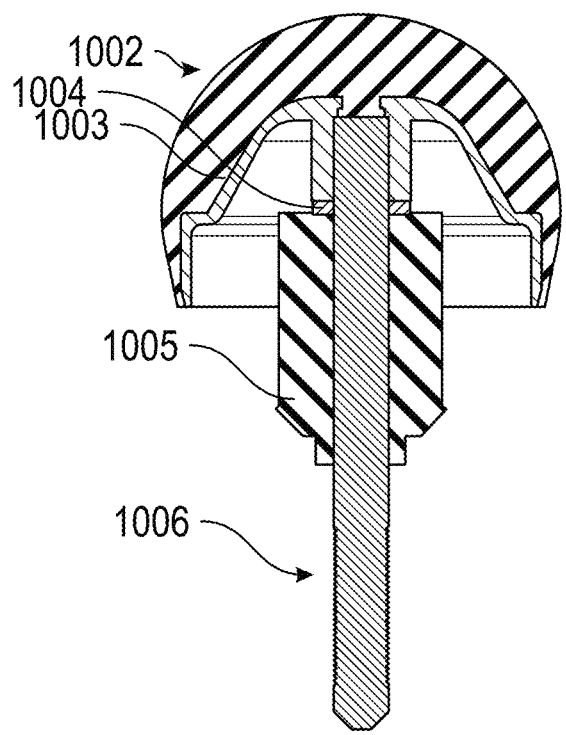

FIGS. 10A and 10B show the assembly 1001 and the cross-sectional view of the femoral neck and head parts of an implant. Femoral head 1002 is made of bio-compatible plastic such as polyethylene, polyether ether ketone (PEEK) or ultra-high-molecular-weight polyethylene (UHMWPE). The plastic femoral head 1002 is injection or compression molded onto the femoral head base 1003 made of a bio-compatible metal such as cobalt, chromium, titanium or medical grade stainless steel 316. A washer 1004 and a plastic reinforcer 1005 are introduced to further increase the stiffness of femoral neck rod 1006.

Figure 11:
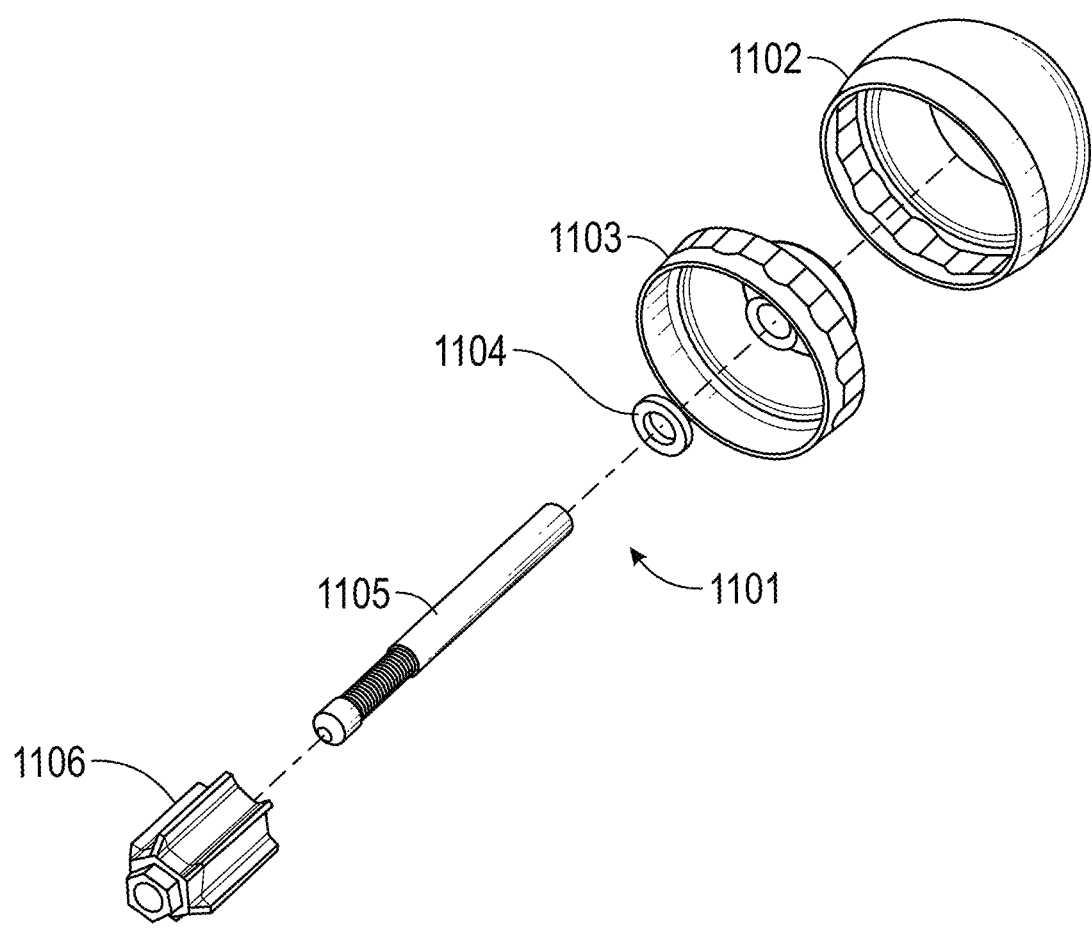
FIG. 11 is an exploded view of the femoral head part.

FIG. 11 shows the exploded view of the femoral head part 1101. It consists of femoral head 1102, femoral head base 1103, washer 1104, reinforcer 1106 and femoral neck rod 1105. Reinforcer 1106 is made of bio compatible plastic like polyethylene. It aids an increase of the stiffness of the femur neck rod 1105 inside the bone by the use of bone segments. Most of the surface that makes contact with cortical and cancellous bone must be covered with bone cement. As a result, high stiffness and stability of the femoral head part onto femoral neck and head anatomy can be obtained by having composite characteristic construction. Thus, this invention accommodates all the age groups of patients even those who may not have strong and high dense bone.

Figure 12:
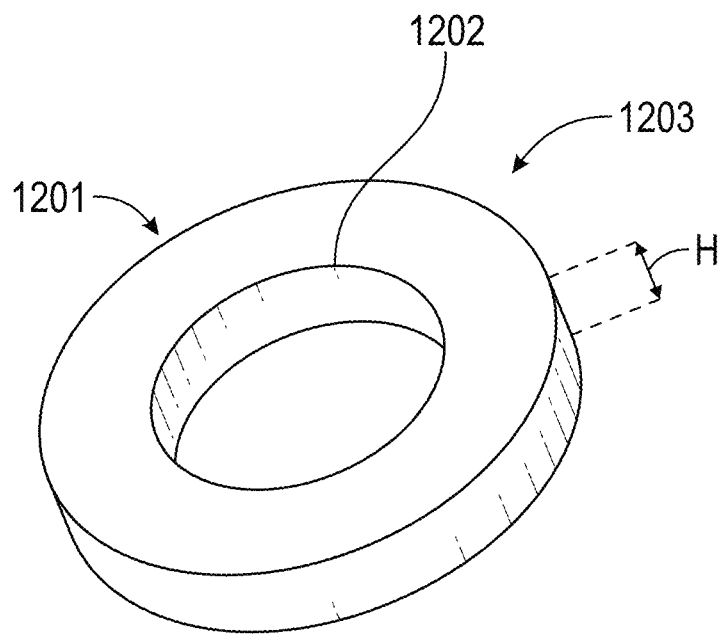
FIG. 12 is a perspective view of a washer for the femoral neck to control the reinforcing length.

FIG. 12 shows a washer 1201 with a thickness or height H in any of several different possible sizes (e.g. H=2 mm, 4 mm, 6 mm, or 8 mm). Such a washer can be used for the washer 1104 in FIG. 11. The washer consists of a disc bounded by two circular edges, an outer one 1203 and an inner one 1202, whose dimensions match with femoral head base features. Depending on the femoral neck characteristics, the height of washer H ranges from 2 to 8 mm and is used to control the reinforcing length; thus, controlling the additional increase of the stiffness femoral neck feature.

Figure 13A:
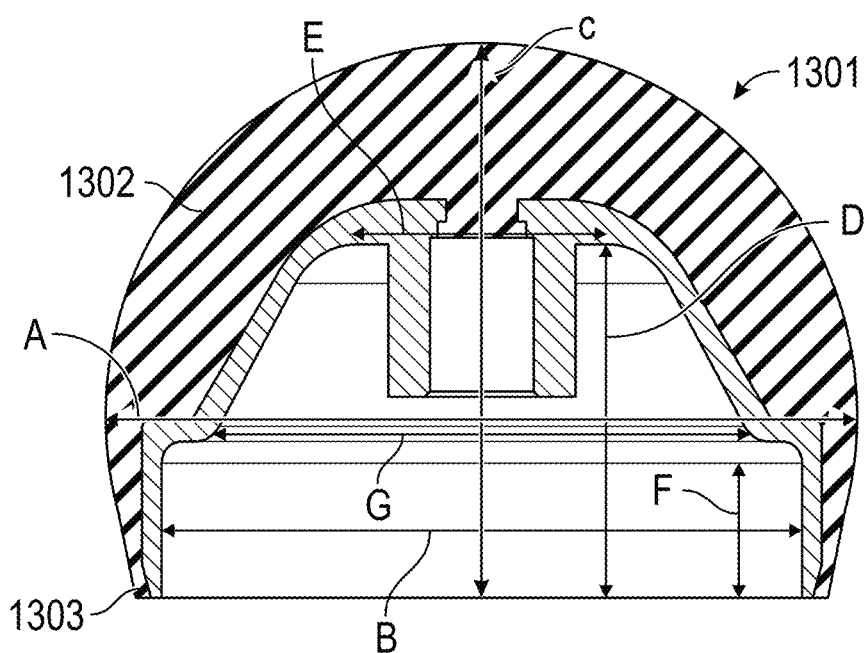
FIGS. 13A and 13B is a sectional view and a side view of the femoral head cap fitting to the femoral head base.
Figure 13B:
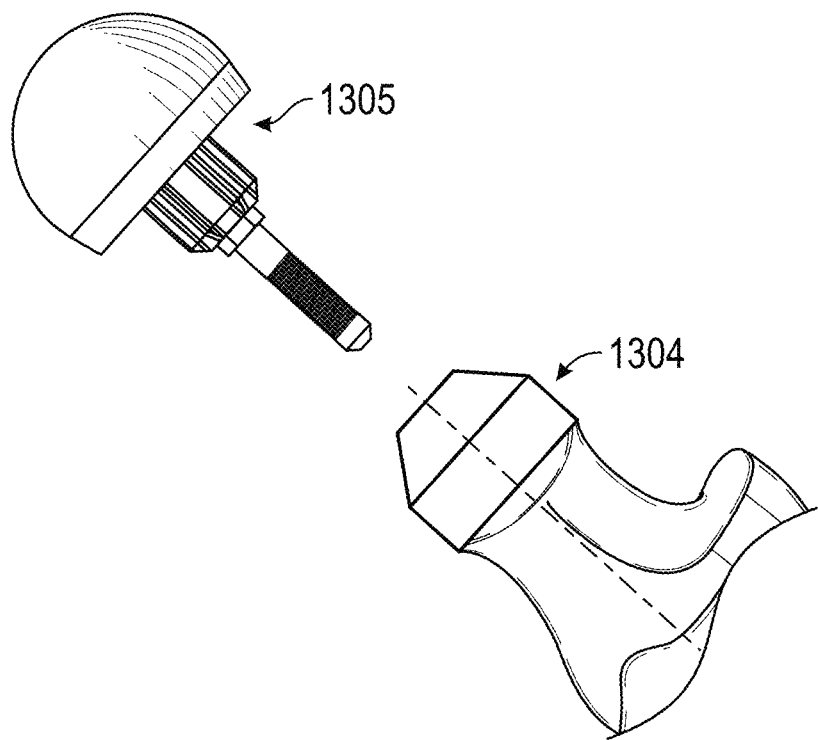

FIGS. 13A and 13B show representative dimensions of the femur head part 1301. It is noted that anatomical femoral head should be shaped to match the inner surface of femoral head base 1303. The shape of this design will help the head part 1305 of the implant seats perfectly on the femoral head bone 1304. One of the innovative parts of this design is the use of plastic for the femoral head cap 1302. The femur head cap may be fitted into the femur head base 1303 by an injection- or compression-molding process. The previous hip resurfacing implant is metal-to-metal contact. Unlike metal-to-metal implant, the plastic-to-metal contact implant requires an additional thickness of the plastic part since the plastic part has a higher wear rate compared with metal. On the other hand, the shape 1304 on anatomical femoral head should be made for stable and strong mating with the femoral head part 1301 under dynamic body loading. The parameters B/A (=0.86±0.005), D/C(=0.65±0.005), E/B (=0.85±0.005), F/D (=0.4±0.005), and G/A (=0.76±0.005) of the design are constant and depend on the diameter of femoral head.

Figure 14:
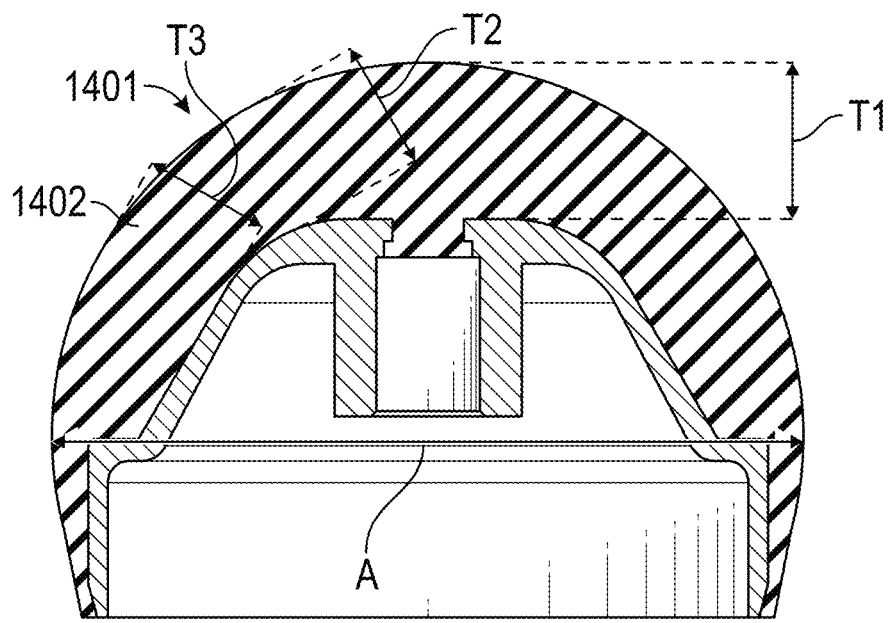
FIG. 14 is a side view of the femoral head part illustrating dimensional ratios.

FIG. 14 shows dimensional ratios of the plastic thickness for the femoral head part 1401. The femoral head 1402 has three thicknesses of the center ratio T1, mid ratio T2 and side ratio T3. For example, T1/A=0.21±0.005, T2/A=0.18±0.005, and T3/A=0.17±0.005. This design comfortably covers potential loading surface on the femoral head plastic with enough plastic thickness while the inner femoral head metal base assures the stable fitting onto the shaped anatomical femoral head as shown in FIG. 13.

Figure 15:
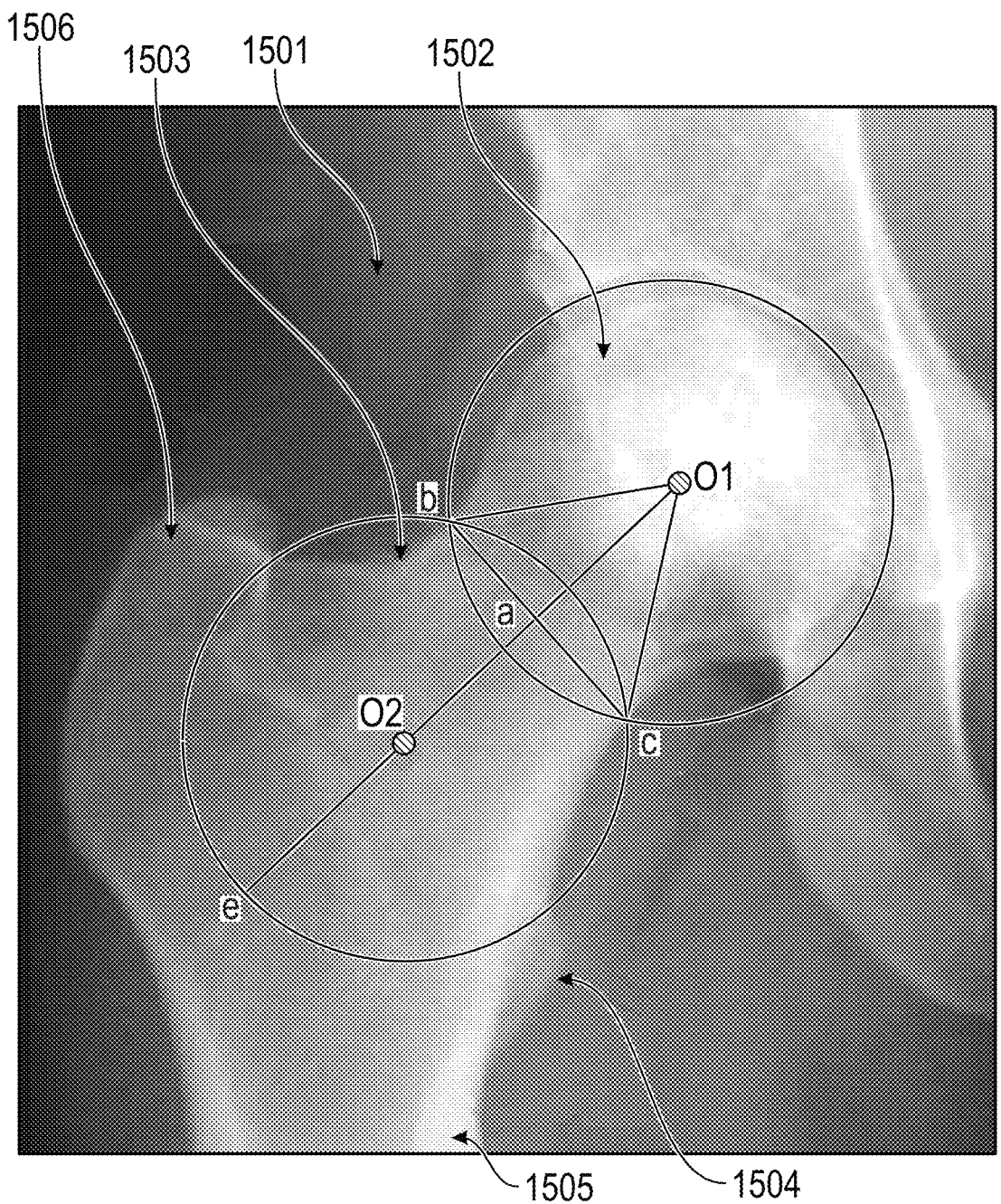
FIG. 15 is an x-ray image of the hip and pelvis illustrating dimensions relevant to the size of the implant features.

FIG. 15 shows an x-ray image of the hip and pelvis 1501. The two circles with the center O1 and O2 have the same diameter of the femoral head 1502. The line going through the point O1 and O2 coincides with the femoral neck rod direction as shown in the previous figures. The points b and c are considered as impinging points and the line be represents impinging line on the femoral neck 1503. And the two circles simultaneously intersect both points b and c. To ensure that the femoral neck rod will intersect the main body shaft and that the main body shaft will be positioned approximately in the middle of the anatomical femoral shaft 1505, the femoral neck rod should pass the area covered between greater trochanter zone 1506 and lesser trochanter 1504. With the information from the diagram in FIG. 15, the femoral neck rod length (preferably length of $O_1$ to e) and reinforcer diameter (preferably length of b to c) can be estimated.

FIG. 16 shows three sets of MRI slices in coronal, axial and sagittal views which illustrate the peculiar anatomical shape relating to the impinging line as introduced in FIG. 15:

1) The MRI slices of coronal 1 and axial 1 point to the position at the femoral head. The MRI slice of sagittal 1 clearly shows the cross-section view of the circle shape.

2) The MRI slices of coronal 2 and axial 2 point to the position near the impinging line. The MRI slice of sagittal 2 also shows the cross-section view of the circle shape despite the smaller diameter than the sagittal 1 MRI slice.

3) The MRI slices of coronal 3 and axial 3 point to the position passing the impinging line and approaching the region of greater trochanter zone 1506 to lesser trochanter 1504. The MRI slice of sagittal 2 also shows the cross-section view of the approximately corner round rectangular shape.

This provides the structural transition information around the impinging line that the structure shown in MRI slice of sagittal 3 view is a base supporting body of femoral head.

Therefore, the reinforcing part as illustrated in the previous figure should pass through the impinging line as much as possible. This length is controlled by the length of the washer part in FIG. 12.

FIG. 17 shows the femoral ball and socket implant 1701. The radius of the femoral head part 1702 is R. There are some relations between this radius and the length of the femoral neck 1703 as shown in the equation for L:

$$L=L_1+L_2=R\cdot(2\cos\varphi+1.45),$$

where $\varphi$ is defined in FIG. 15 and $\varphi=35°$ (median value). $L_2$ is called the implant femoral neck distance. $L_1/R=0.45\pm0.005$ and $L_2/R=1+2\cos\varphi$. Therefore, $L=3.1R$.

FIGS. 18A and 18B show a reinforcer component 1801 made of a bio-compatible plastic like polyethylene. To preserve more cancellous bone with an increase the stiffness, fins 1803 are introduced with diameter D and sizing factor N. The diameters of T and r have compatible dimensions to the femoral head base dimensions and femoral neck rod diameter. The inner circle can be inserted by either tight fitting or threading. To preserve more cancellous bone around femoral neck, a sizing factor N of 0.75 may be used for the design. The diameter of D is function of R (radius of femoral head) and the two sizes of reinforcing parts are introduced to cover most of the patients with $\varphi=33°$ and $37°$, where $\varphi$ is as defined above for FIG. 15. $D=2N\cdot R\cdot\sin 33°=1.09NR$ or $D=2N\cdot R\cdot\sin 37°=1.203NR$. The choice of $33°$ or $37°$ angle is determined by the reinforcer to make sure that the fin feature does not make contact the cortical bone with the sizing factor N of 0.75. The femur will be drilled with radius r and broached to provide space for fin shape 1803 of the reinforcer 1804. The bone cement is applied to the outer surface of the reinforcer 1801. Cancellous bone, bone cement, plastic reinforcer and the metal femoral neck rod work together as a composite that fits the implant tightly inside the femur. Also, the overall length S of reinforcer 1804 is determined by taking upper bound angle $40°$. $S=R\cdot\cos 40°=0.766R$.

Figure 19:
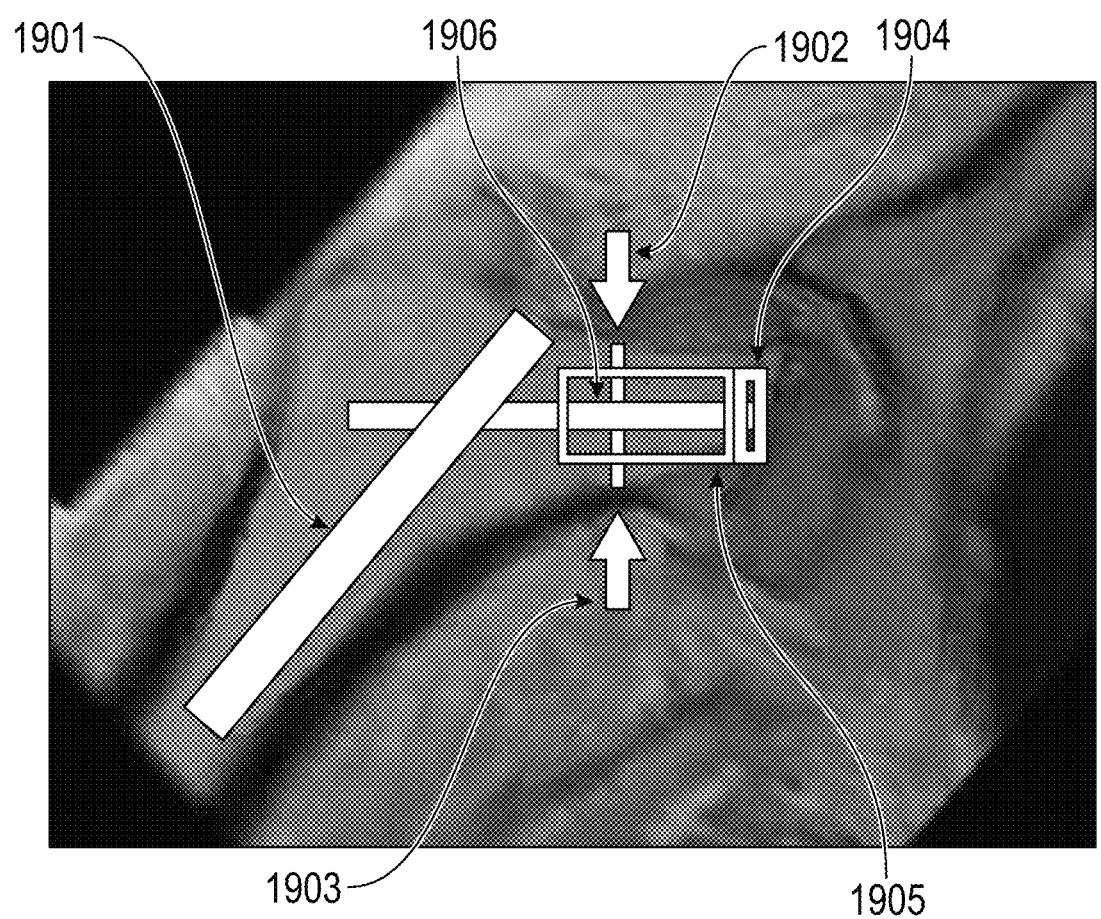
FIG. 19 is a coronal MRI slice image of the proximal femur overlaid with the desired implant position.

FIG. 19 shows a coronal MRI slice of the proximal femur 1902 with the desired implant position. The femoral neck rod positioned to the center line of the femoral neck feature shown in FIG. 15. The reinforcer 1905 fixed on the femoral neck rod 1906 passes the impinging line 1903 and close to the femoral main body shaft with an aid of the washer 1904.

Figure 20A:
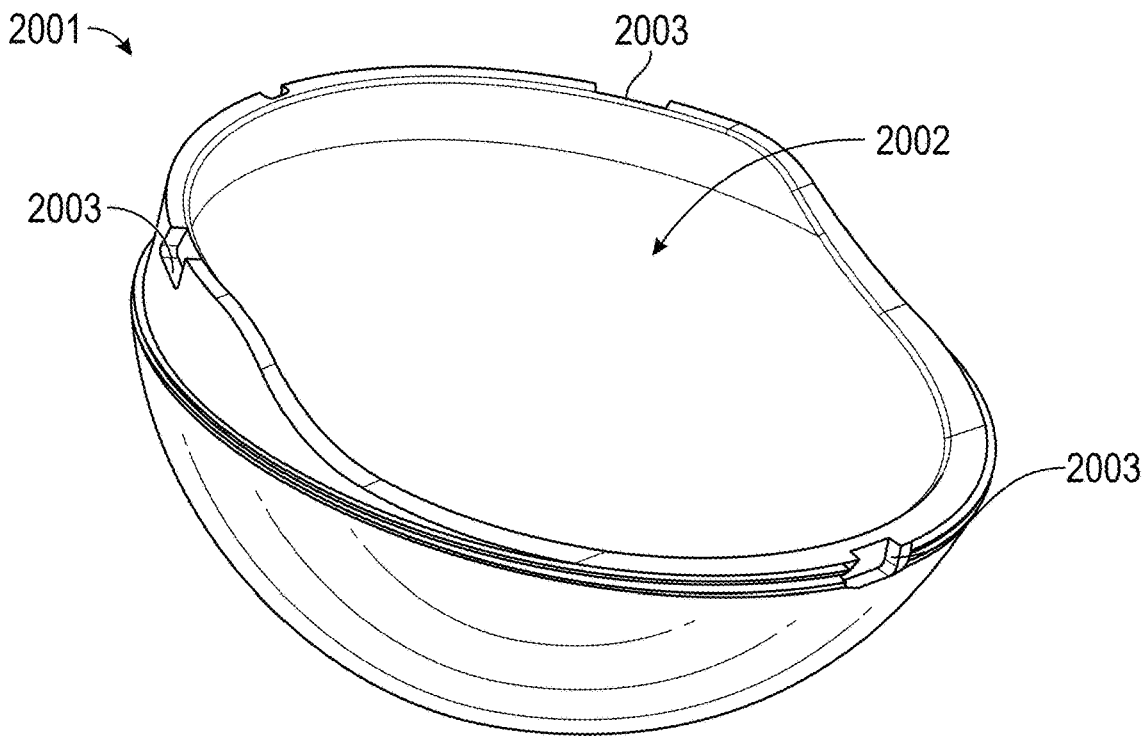
FIGS. 20A-20C are perspective, side, and front views of an acetabular cup of the implant.
Figure 20B:
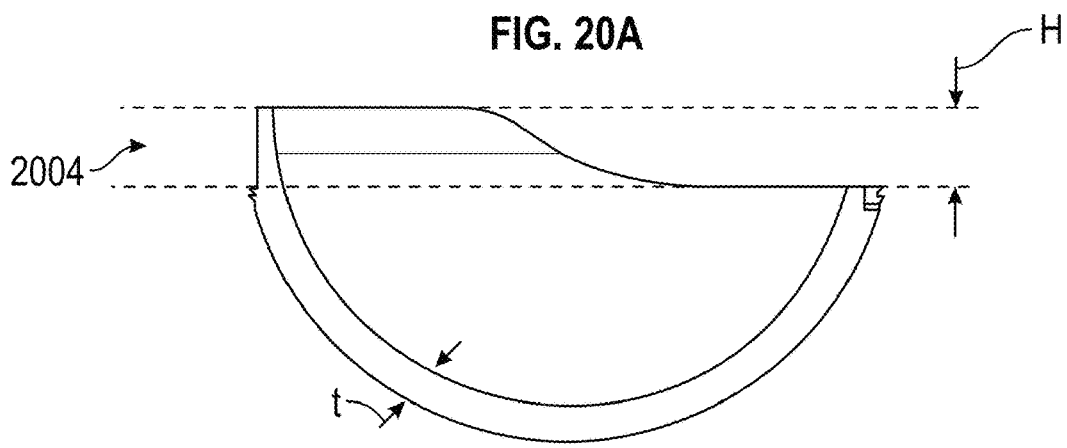
Figure 20C:
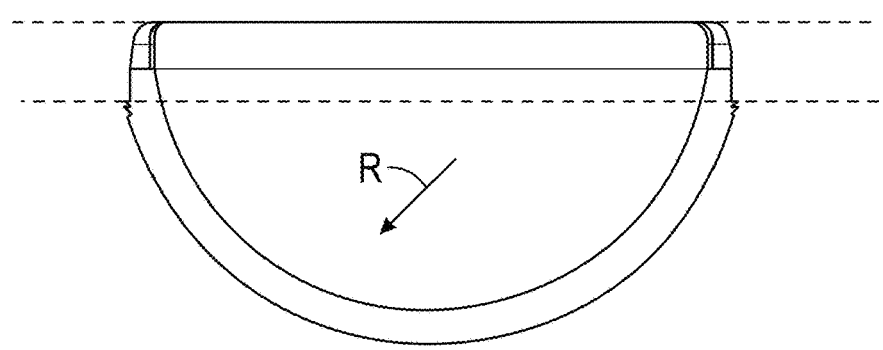

FIGS. 20A-20C show a metal acetabular cup 2001. The acetabular cup 2001 may be made from a bio-compatible metal, such as cobalt, chromium, titanium, alloys thereof, and medical-grade stainless steel 316. It consists of an inner sphere surface 2002 that mates with the plastic femoral head. The three holding notches 2003 which are used for placement of the acetabular cup 2001 inside the acetabular anatomy of the hip. The thickness of the acetabular cup is t and the radius of the inner sphere is R. H is the height of the acetabular wall 2004 which prevents the implant from dislocation. The height is defined as $H=R/(3.7)$.

Figure 21:
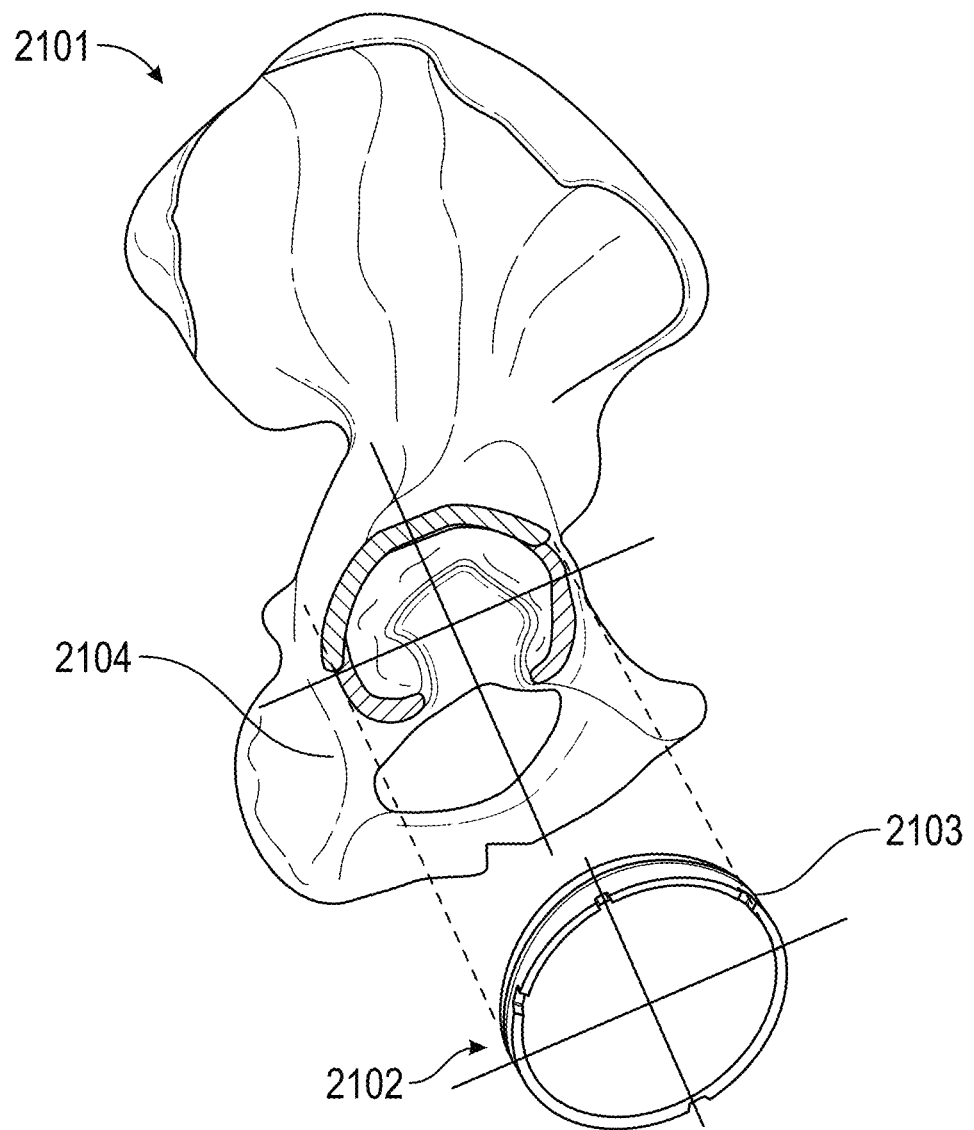
FIG. 21 is a perspective view showing insertion of the acetabular cup into an acetabulum anatomy of the pelvis.

FIG. 21 shows the directional property 2101 of the acetabular cup positioning 2102 which seats inside the pelvis. The lines represent the boundary of the acetabular labrum 2104, including the superior acetabular labrum where usually the most dislocations can happen. In this invention, an acetabular wall 2103 may be introduced into this area to prevent any dislocation problems.

Figure 22:
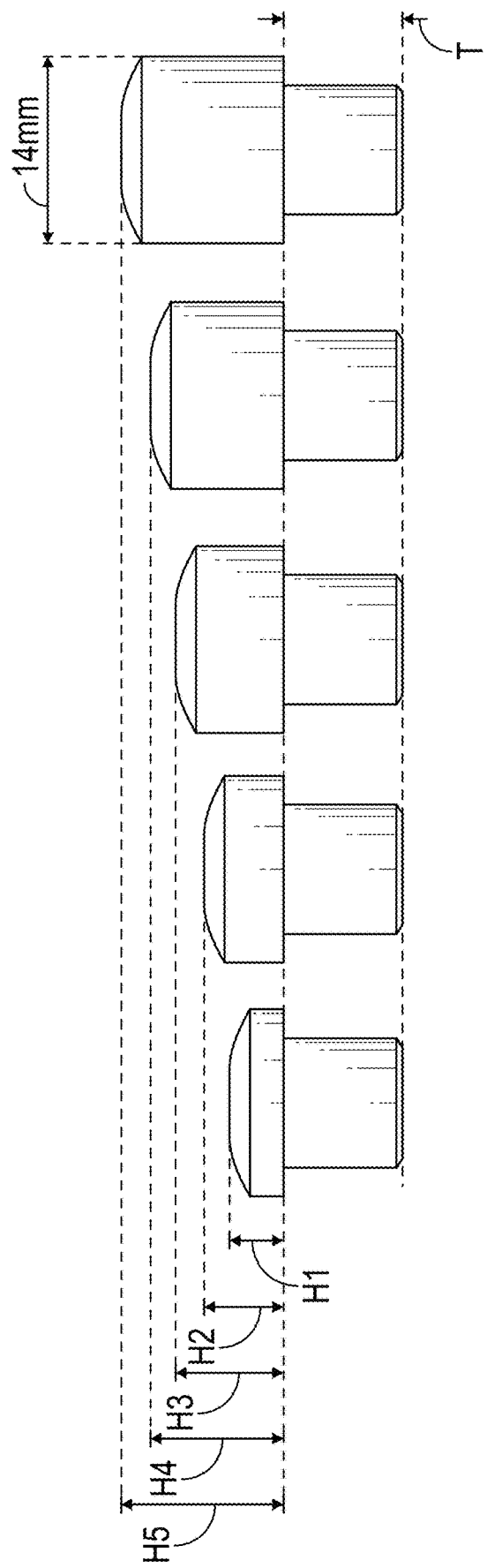
FIG. 22 is a side view of various sized top cover secured locks for the implant.

As shown in FIG. 22 and the following table, the sizes for the top cover secured lock may vary from 1 to 5 to ensure that the top cover is exposed just above greater trochanter as illustrated in the previous figures. A diameter of 14 mm is the same for all sizes.

| SIZE | H (mm) | T (mm) |
|---|---|---|
| 1 | 4 | 8.4 |
| 2 | 6 | 8.4 |
| 3 | 8 | 8.4 |
| 4 | 10 | 8.4 |
| 5 | 12 | 8.4 |

Figure 23:
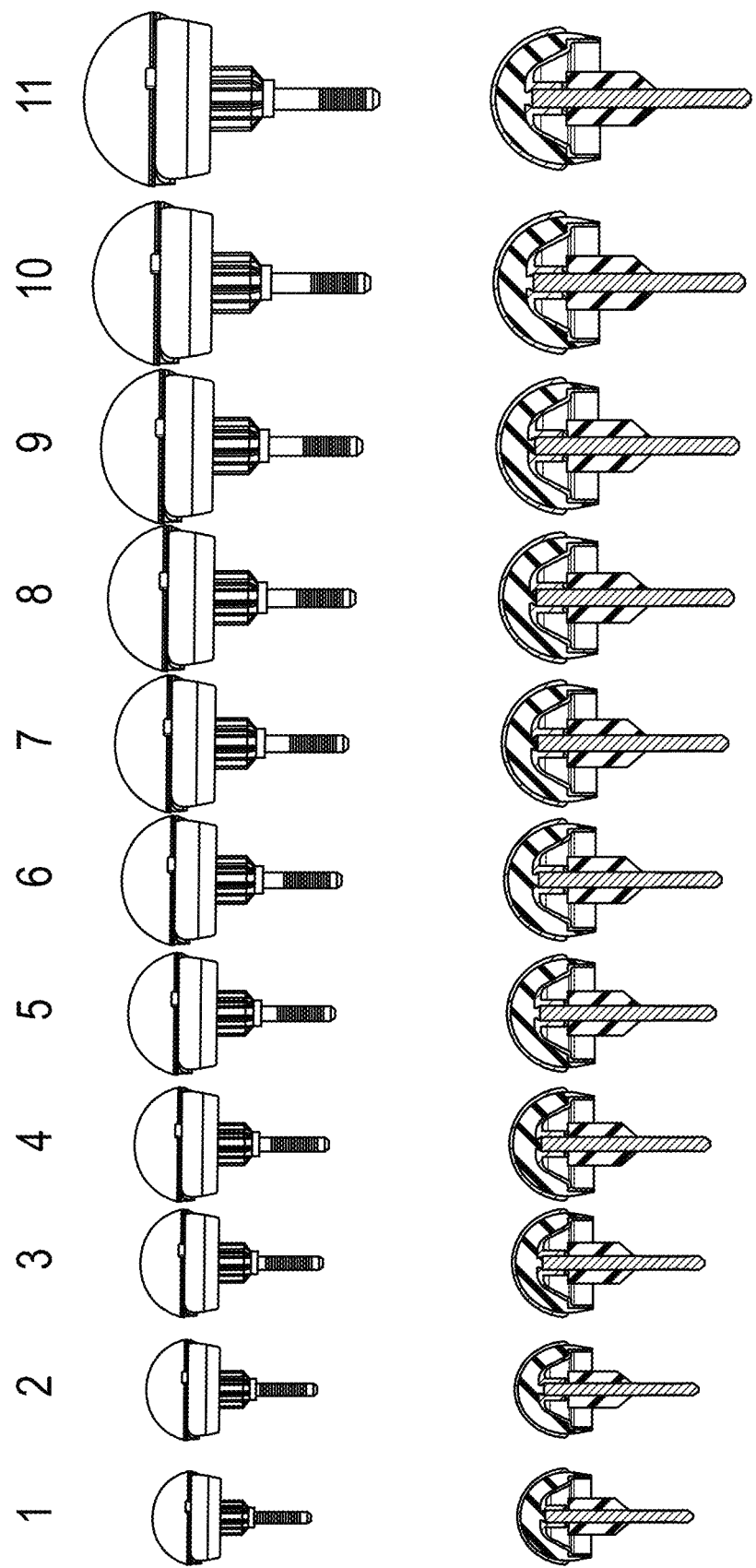
FIG. 23 is a side and side sectional view of various sized femoral head parts of the implant.

As shown in FIG. 23 and the following table, the implant femoral head part may vary from size 1 to 11 to accommodate all age groups of clients.

| Size | Femoral Head Diameter (mm) |
|---|---|
| 1 | 38.5 |
| 2 | 40.5 |
| 3 | 42.5 |
| 4 | 44.5 |
| 5 | 46.5 |
| 6 | 48.5 |
| 7 | 50.5 |
| 8 | 52.5 |
| 9 | 54.5 |
| 10 | 56.5 |
| 11 | 58.5 |

Figure 24:
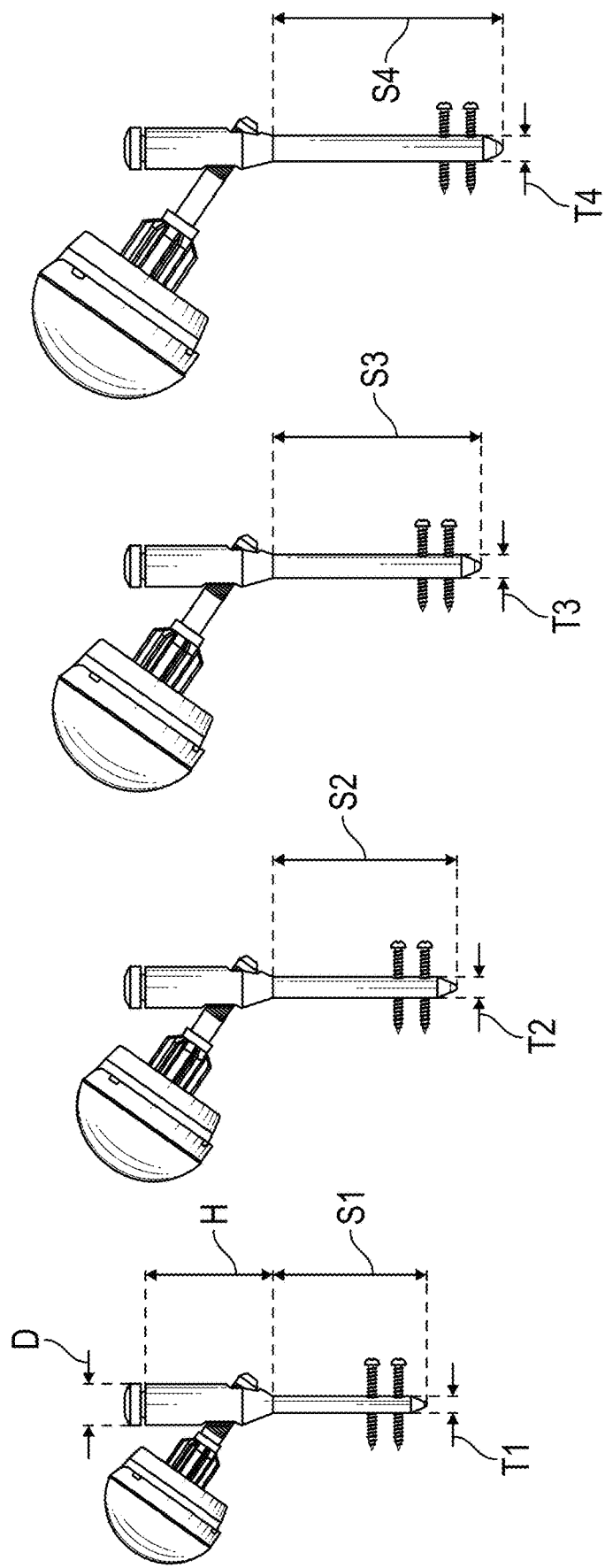
FIG. 24 is a side view of various sized main body shaft components of the implant.

FIG. 24 illustrates representative femoral shaft dimensions for the main body shaft component. The upper portion of the main body shaft (dimensions H and D) is constant regardless of the sizes, as seen in the following table.

| SIZE | T (mm) | S (mm) | H (mm) | D (mm) |
|---|---|---|---|---|
| 1 | 7.3 | 62.5 | 46.5 | 14.0 |
| 2 | 8.1 | 71.5 | 46.5 | 14.0 |
| 3 | 9 | 80.5 | 46.5 | 14.0 |
| 4 | 10.5 | 88.5 | 46.5 | 14.0 |

With reference to FIGS. 25A, 25B and 25C, an alternative metallic femoral head base 2301 has several stabilizer features to aid secure polymer-to-metal bonding of the femoral head surface onto the femoral head base. Specifically, a set of dimples 2302 are provided in the surface of the femoral head base 2301. An additional set of larger dimples 2303 are provided around the periphery of the femoral head base 2301. Finally, a set of shallow mounds 2304 around the periphery of the femoral head base 2301 stabilize the femoral head against rotational forces. Together, these stabilizer features create a stable interface between the polymer femoral head surface and the metallic femoral head base. Also seen in FIG. 25C is a joining thread 2305 that is used to connect the tapered femoral neck rod to the femoral head.

FIGS. 26A, 26B and 26C show close-up views of an alternative femoral head base 2401 with attention to features on its interior surface that aid in bonding that base 2401 to a patient's bone. Specifically, as seen in the enlarged portion 2402, there are 0.5 mm deep dimples 2403 on the interior periphery into which bone cement can be applied. One of the shallow mounds on the outer periphery of the base 2401 can also be seen in the enlarged portion 2402.

Figure 27:
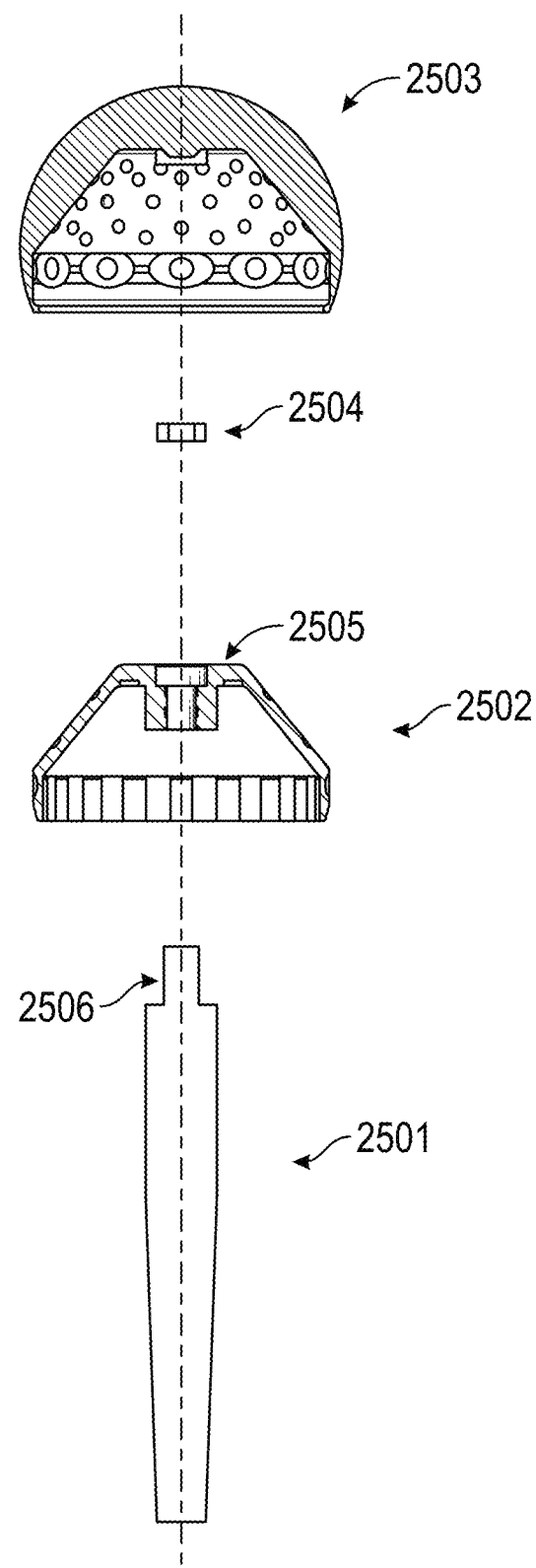
FIG. 27 is an exploded view of the alternative femoral and neck parts of the implant.

The exploded view in FIG. 27 shows attachment of a femoral neck rod 2501 to the alternative femoral head base 2502 and femoral head 2503. The femoral neck thread 2506 on the end of the femoral neck rod 2501 is joined via internal threads 2505 of the femoral head base 2502 and a securing nut 2504 is used to double-secure the resulting joint. The polymer femoral head 2503 is compression molded onto the femoral head base 2502 after the neck is attached. The femoral neck rod 2501 may have a tapered shaft, e.g. with a two-degree taper that slowly narrows away from the femoral head attachment end.

What is claimed is:

1. A hip implant, comprising:
    an acetabular cup configured to be inserted into an acetabulum anatomy of a pelvis, the acetabular cup composed of a bio-compatible metal;
    a femoral head and neck portion with a femoral head composed of a bio-compatible polymer molded onto a bio-compatible metal femoral head base that is attached to a bio-compatible metal femoral neck rod, the femoral head configured to interface with the acetabular cup as a smooth plastic-to-metal spherical-surface joint, the femoral neck rod configured to be inserted along a center line into a neck of the femur, the femoral neck rod having a zigzag surface in a contact area; and
    a main body shaft configured to be inserted into a femoral shaft region of the femur and secured by bone screws through cortical bone of the femur, the main body shaft composed of a bio-compatible metal and having a linear central axis that extends an entire length of the main body shaft, the main body shaft also having a curved diagonal hole therethrough located at the center line of the neck of the femur so as to receive the femoral neck rod at an angle adjustable to align with center line of the neck, the main body shaft further having a secured lock mechanism insertable into the main body shaft above the diagonal hole with an angle adjustment joint mechanism screwed down to engage the femoral neck rod in the contact area, the secured lock mechanism crushing the zigzag surface of the femoral neck rod in the contact area.

2. The hip implant as in claim 1, wherein the bio-compatible metal comprises any of cobalt, chromium, titanium, alloys thereof and medical-grade stainless steel 316.

3. The hip implant as in claim 1, wherein the bio-compatible polymer comprises any of polyethylene, polyether ether ketone (PEEL), and ultra-high-molecular-weight polyethylene (UHMWPE).

4. The hip implant as in claim 1, further comprising a washer for the femoral neck rod with a thickness selected for positioning the femoral head and neck portion.

5. The hip implant as in claim 1, further comprising a femoral neck reinforcer for insertion around the femoral neck rod at a location corresponding to the neck of the femur.

6. The hip implant as in claim 1, wherein the adjustable angle of the femoral neck rod received in the curved diagonal hole of the main body shaft ranges from 40° to 70° relative to the linear central axis of the main body shaft.

7. The hip implant as in claim 1, wherein the femoral head base has a set of stabilizer features on its surface providing a secure interface with the femoral head.

8. The hip implant as in claim 7, wherein the stabilizer features of the femoral head base comprise a set of dimples over its surface and into which the femoral head is molded.

9. The hip implant as in claim 7, wherein the stabilizer features of the femoral head base comprise a set of raised mounds distributed around a radial perimeter of the head base and against which the femoral head is molded.

10. A hip implant, comprising:
    an acetabular cup configured to be inserted into an acetabulum anatomy of a pelvis, the acetabular cup composed of a bio-compatible metal;
    a femoral head and neck portion with a femoral head composed of a bio-compatible polymer molded onto a bio-compatible metal femoral head base that is attached to a bio-compatible metal femoral neck rod, the femoral head configured to interface with the acetabular cup as a smooth plastic-to-metal spherical-surface joint and having selected polymer dimensions and dimensional ratios corresponding to dynamic body loading in a patient, the femoral neck rod configured to be inserted along a center line into a neck of the femur, a femoral neck reinforcer being provided for insertion around the femoral neck rod at a location corresponding to the neck of the femur, the femoral neck rod further having a zigzag surface in a contact area; and
    a main body shaft configured to be inserted into a femoral shaft region of the femur and secured by bone screws through cortical bone of the femur, the main body shaft composed of a bio-compatible metal and having a linear central axis that extends an entire length of the main body shaft, the main body shaft also having a curved diagonal hole therethrough located at the center line of the neck of the femur so as to receive the femoral neck rod at an adjustable angle relative to the linear central axis of the main body shaft so as to align with center line of the neck, a secured lock mechanism being insertable into the main body shaft above the diagonal hole with an angle adjustment joint mechanism screwed down to engage the femoral neck rod in the contact area, the secured lock mechanism crushing the zigzag surface of the femoral neck rod in the contact area.

11. The hip implant as in claim 10, wherein the bio-compatible metal comprises any of cobalt, chromium, titanium, alloys thereof and medical-grade stainless steel 316.

12. The hip implant as in claim 10, wherein the bio-compatible polymer comprises any of polyethylene, polyether ether ketone (PEEL), and ultra-high-molecular-weight polyethylene (UHMWPE).

13. The hip implant as in claim 10, wherein the femoral head base has a set of stabilizer features on its surface providing a secure interface with the femoral head.

14. The hip implant as in claim 13, wherein the stabilizer features of the femoral head base comprise a set of dimples over its surface and into which the femoral head is molded.

15. The hip implant as in claim 13, wherein the stabilizer features of the femoral head base comprise a set of raised mounds distributed around a radial perimeter of the head base and against which the femoral head is molded.

\* \* \* \* \*